US012572207B2

(12) United States Patent
Goenka et al.

(10) Patent No.: US 12,572,207 B2
(45) Date of Patent: Mar. 10, 2026

(54) SYSTEM AND METHOD FOR ADAPTIVE USER INTERFACE CONTROL BASED UPON EMOTIONAL STATE

(71) Applicant: Yahoo Assets LLC, New York, NY (US)

(72) Inventors: Mohit Goenka, Santa Clara, CA (US); Gnanavel Shanmugam, San Jose, CA (US); Nikita Varma, Milpitas, CA (US); Ashish K Dharamshi, Sunnyvale, CA (US)

(73) Assignee: Yahoo Assets LLC, New York, NY (US)

( * ) Notice: Subject to any disclaimer, the term of this patent is extended or adjusted under 35 U.S.C. 154(b) by 0 days.

(21) Appl. No.: 18/767,631

(22) Filed: Jul. 9, 2024

(65) Prior Publication Data

US 2026/0016893 A1     Jan. 15, 2026

(51) Int. Cl.
*G06F 3/01*     (2006.01)
*A61B 5/16*     (2006.01)

(52) U.S. Cl.
CPC .............. *G06F 3/015* (2013.01); *A61B 5/165* (2013.01)

(58) Field of Classification Search
CPC .......................... G06F 3/01–017; A61B 5/165
See application file for complete search history.

(56) References Cited

U.S. PATENT DOCUMENTS

| | | | | |
|---|---|---|---|---|
| 2011/0004047 A1* | 1/2011 | Braspenning | ............ | A61B 5/16 600/27 |
| 2013/0331132 A1* | 12/2013 | Goliszewski | ........... | H04W 4/12 455/466 |
| 2023/0079716 A1* | 3/2023 | Sambhwani | ........... | H04R 27/00 381/303 |

* cited by examiner

*Primary Examiner* — Hang Lin
(74) *Attorney, Agent, or Firm* — Cooper Legal Group LLC

(57)     ABSTRACT
In accordance with the present disclosure, one or more computing devices and/or methods are provided. In an example, an emotional state of a user may be determined based upon one or more signals generated by one or more sensors and/or user activity of the user. A communication interface may be controlled based upon the emotional state.

20 Claims, 14 Drawing Sheets

DETERMINE EMOTIONAL STATE OF USER BASED UPON ONE OR MORE SIGNALS GENERATED BY ONE OR MORE SENSORS, AND/OR USER ACTIVITY OF THE USER — 402

CONTROL COMMUNICATION INTERFACE BASED UPON EMOTIONAL STATE — 404

501 ⟍

500

Figure 5C:
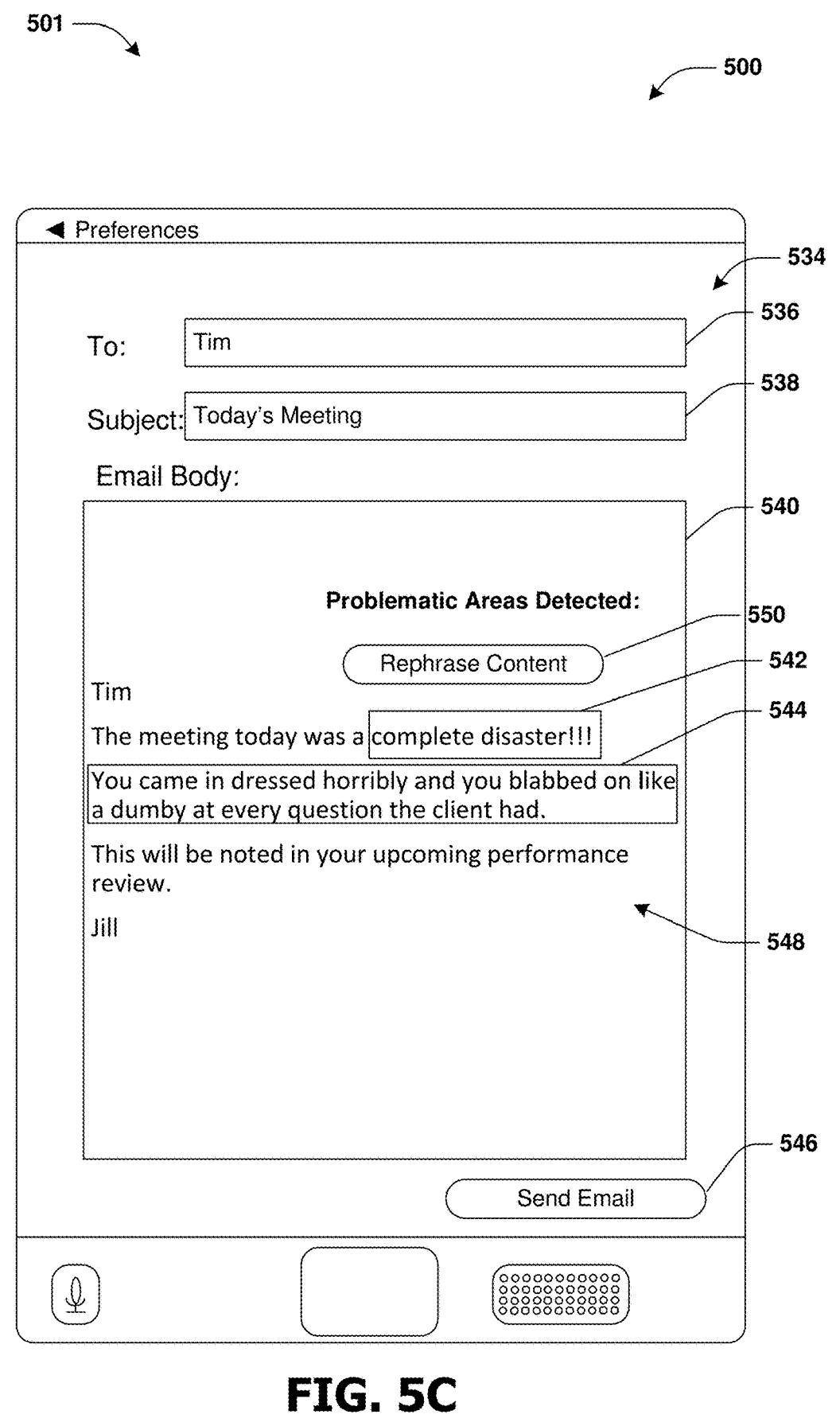

501 ⟍

500 ⟍

◄ Preferences

534

To:   | Tim |   536

Subject: | Today's Meeting |   538

Email Body:

540

Problematic Areas Detected:

550

( Rephrase Content )   542

Tim

544

The meeting today was a | complete disaster!!! |

| You came in dressed horribly and you blabbed on like
a dumby at every question the client had. |

This will be noted in your upcoming performance
review.

Jill

548

546

( Send Email )

501 ⟍

500 ⟍

◀ Preferences

— 534

To:    | Tim |
— 536

Subject: | Today's Meeting |
— 538

Email Body:
— 540

You seem pretty angry right now and sending this email to your coworker may have potential consequences for your career and relationship with coworkers.
— 560
— 561

Recommended Actions:

- Rewrite this email later (after a nap or tomorrow morning)
— 562

- Do a breathing exercise for a few minutes, and rewrite this email afterwards    ( Breathing Exercise Info )
— 564

- Do an activity, and rewrite this email afterwards ( Activity )

- Rewrite this email now with our help     ( Rephrase )
— 563
— 565

Recommended time to rest before continuing activity:    4:46
— 566

( Continue to Composing Email )    ( Override )
— 568    — 570

( Send Email )
— 546

◀ Preferences

—— 534

To:     | Tim |     —— 536

Subject: | Today's Meeting |     —— 538

Email Body:     —— 540

Hi Tim,

I wanted to discuss today's meeting with you. I noticed a few areas where we could improve our approach for future client interactions.

Firstly, ensuring we are dressed in a professional manner is important as it sets the tone for the meeting. Secondly, it might be beneficial to prepare more thoroughly for the questions that the client might ask. This can help us provide clear and confident responses.

I believe addressing these points will help us make a stronger impression in future meetings. Let's discuss this further during our next one-on-one.

Best,

Jill

—— 572

Send Email     —— 546

Figure 5F:
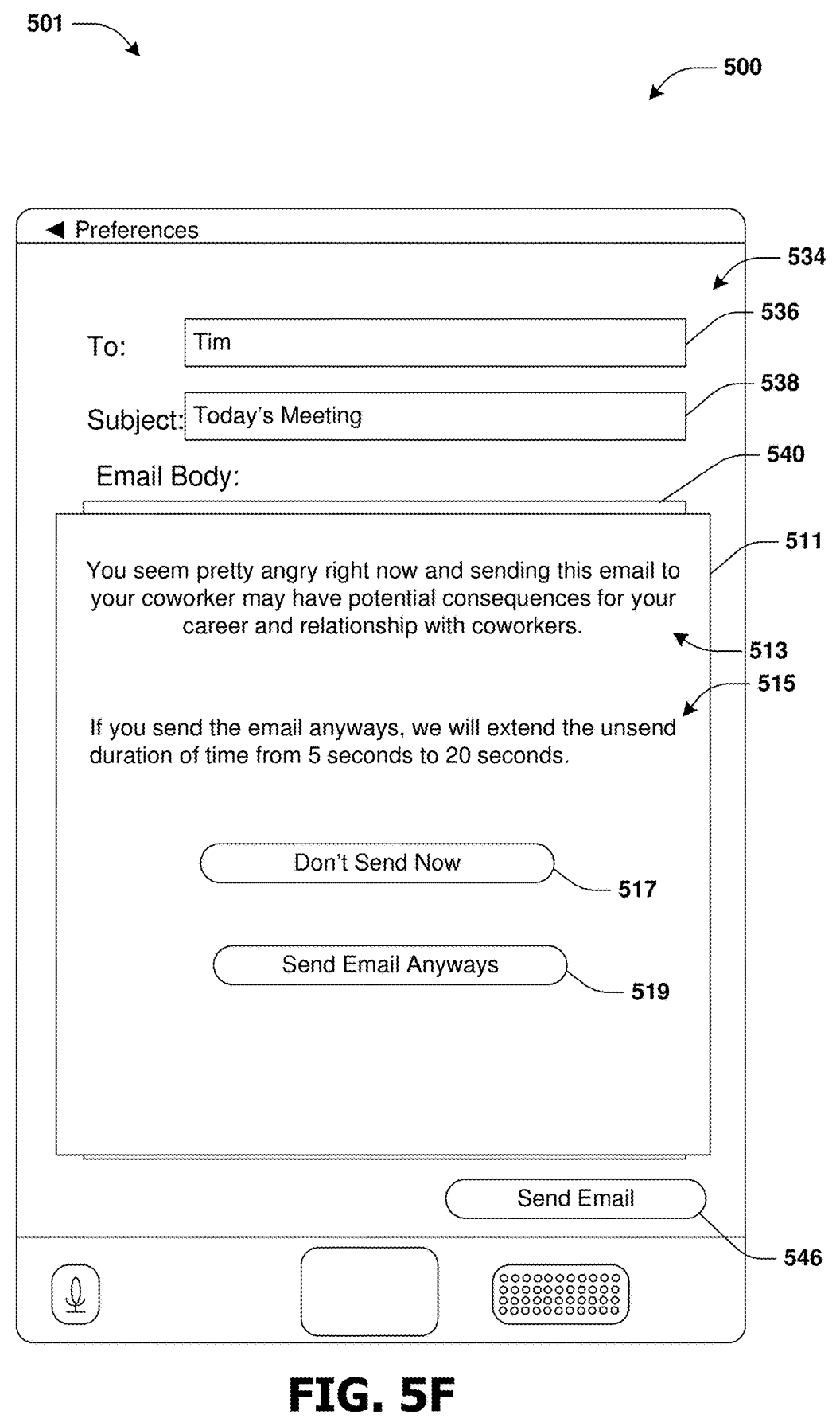

◄ Preferences

— 534

To:     Tim     — 536

Subject: Today's Meeting     — 538

Email Body:     — 540

— 511

You seem pretty angry right now and sending this email to your coworker may have potential consequences for your career and relationship with coworkers.

— 513
— 515

If you send the email anyways, we will extend the unsend duration of time from 5 seconds to 20 seconds.

Don't Send Now     — 517

Send Email Anyways     — 519

Send Email

Figure 5H:
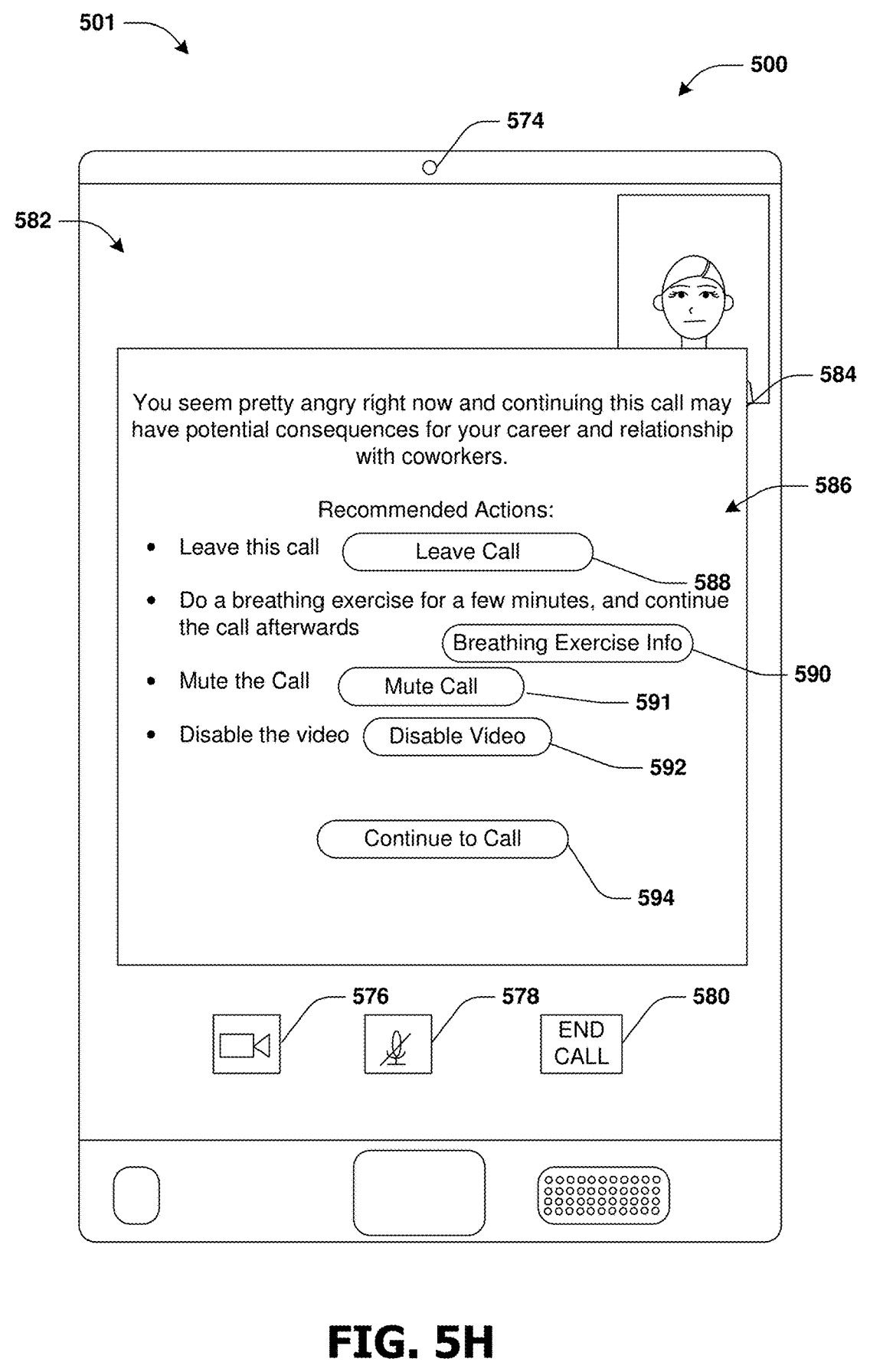

You seem pretty angry right now and continuing this call may have potential consequences for your career and relationship with coworkers.

586

Recommended Actions:

- Leave this call        Leave Call

588

- Do a breathing exercise for a few minutes, and continue the call afterwards

Breathing Exercise Info

590

- Mute the Call        Mute Call

591

- Disable the video        Disable Video

592

Continue to Call

594

576        578        580

END CALL

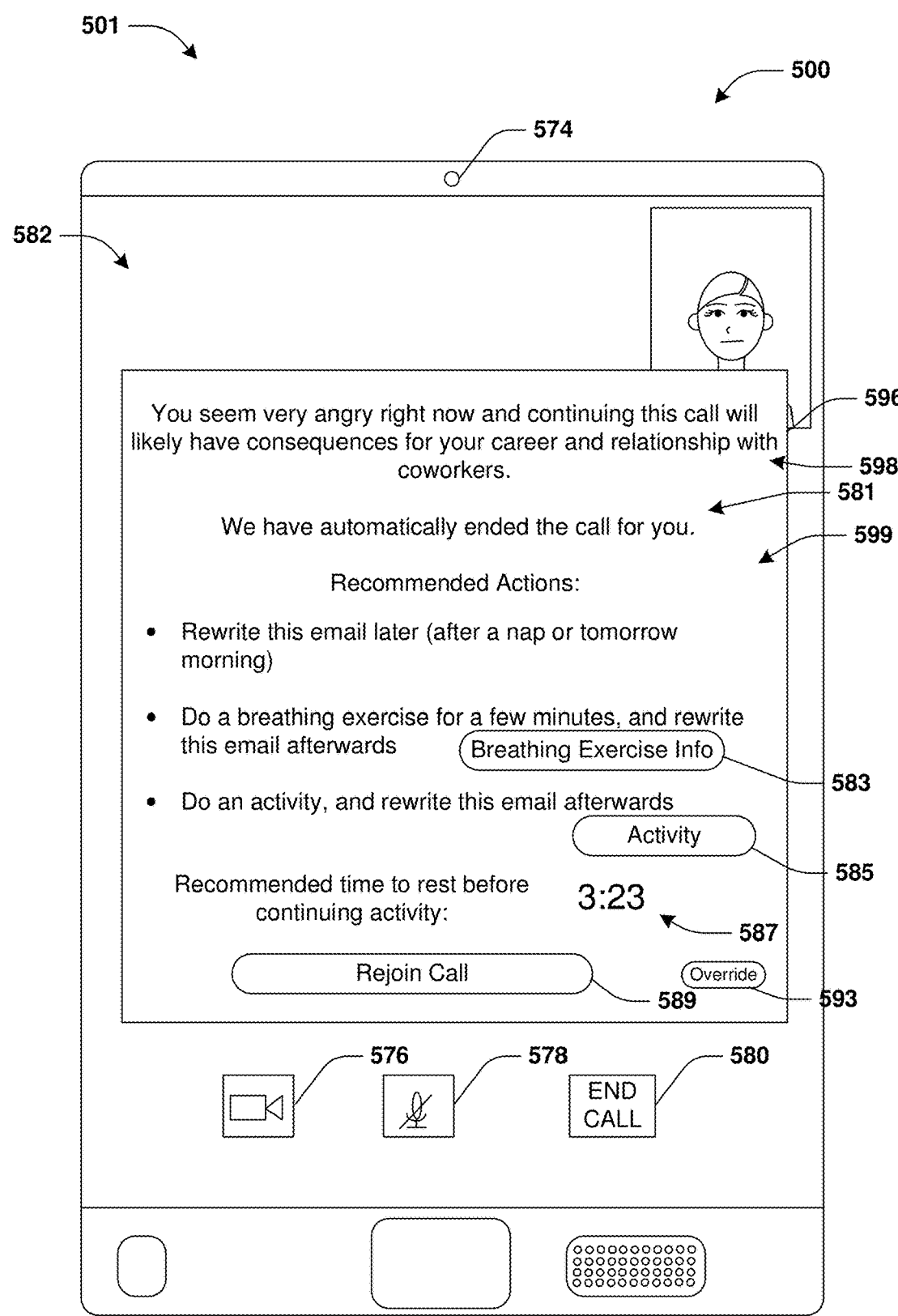

You seem very angry right now and continuing this call will likely have consequences for your career and relationship with coworkers.

We have automatically ended the call for you.

Recommended Actions:

- Rewrite this email later (after a nap or tomorrow morning)

- Do a breathing exercise for a few minutes, and rewrite this email afterwards    Breathing Exercise Info

- Do an activity, and rewrite this email afterwards
    Activity

Recommended time to rest before continuing activity:    3:23

Rejoin Call    Override 596
598
581
599
583
585
587
589
593

576    578    580

END CALL

◄ Preferences

— 534

— 536

To:     | Gregory |

Subject: | Daycare for Janice |

— 538

Email Body:

— 540

Problematic Areas Detected:

— 551

( Rephrase Content )

Hi Gregory

— 543

| I hope you're doing well today.

I'm doing okay. How is work going? |

The Daycare called about Janice. I think you should call me.

Jill

— 549

— 546

( Send Email )

SYSTEM AND METHOD FOR ADAPTIVE USER INTERFACE CONTROL BASED UPON EMOTIONAL STATE

BACKGROUND

Many services, such as websites, applications, etc. may provide platforms for communicating with other users. For example, a user may interact with an email interface to send and/or receive emails, a social network interface to share social media posts, etc.

SUMMARY

In accordance with the present disclosure, one or more computing devices and/or methods are provided. In an example, an emotional state of a user may be determined based upon one or more signals generated by one or more sensors and/or user activity of the user. A communication interface may be controlled based upon the emotional state.

DESCRIPTION OF THE DRAWINGS

While the techniques presented herein may be embodied in alternative forms, the particular embodiments illustrated in the drawings are only a few examples that are supplemental of the description provided herein. These embodiments are not to be interpreted in a limiting manner, such as limiting the claims appended hereto.

FIG. 5C is a component block diagram illustrating an example system for controlling a communication interface based upon an emotional state of a user, where a second communication interface is displayed via a first client device.

FIG. 5D is a component block diagram illustrating an example system for controlling a communication interface based upon an emotional state of a user, where a second communication interface is displayed via a first client device.

FIG. 5E is a component block diagram illustrating an example system for controlling a communication interface based upon an emotional state of a user, where a second communication interface is displayed via a first client device.

FIG. 5F is a component block diagram illustrating an example system for controlling a communication interface based upon an emotional state of a user, where a second communication interface is displayed via a first client device.

FIG. 5H is a component block diagram illustrating an example system for controlling a communication interface based upon an emotional state of a user, where a second communication interface is displayed via a first client device.

FIG. 5I is a component block diagram illustrating an example system for controlling a communication interface based upon an emotional state of a user, where a second communication interface is displayed via a first client device.

DETAILED DESCRIPTION

Subject matter will now be described more fully hereinafter with reference to the accompanying drawings, which form a part hereof, and which show, by way of illustration, specific example embodiments. This description is not intended as an extensive or detailed discussion of known concepts. Details that are known generally to those of ordinary skill in the relevant art may have been omitted, or may be handled in summary fashion.

The following subject matter may be embodied in a variety of different forms, such as methods, devices, components, and/or systems. Accordingly, this subject matter is not intended to be construed as limited to any example embodiments set forth herein. Rather, example embodiments are provided merely to be illustrative. Such embodiments may, for example, take the form of hardware, software, firmware or any combination thereof.

1. Computing Scenario

The following provides a discussion of some types of computing scenarios in which the disclosed subject matter may be utilized and/or implemented.

1.1. Networking

Figure 1:
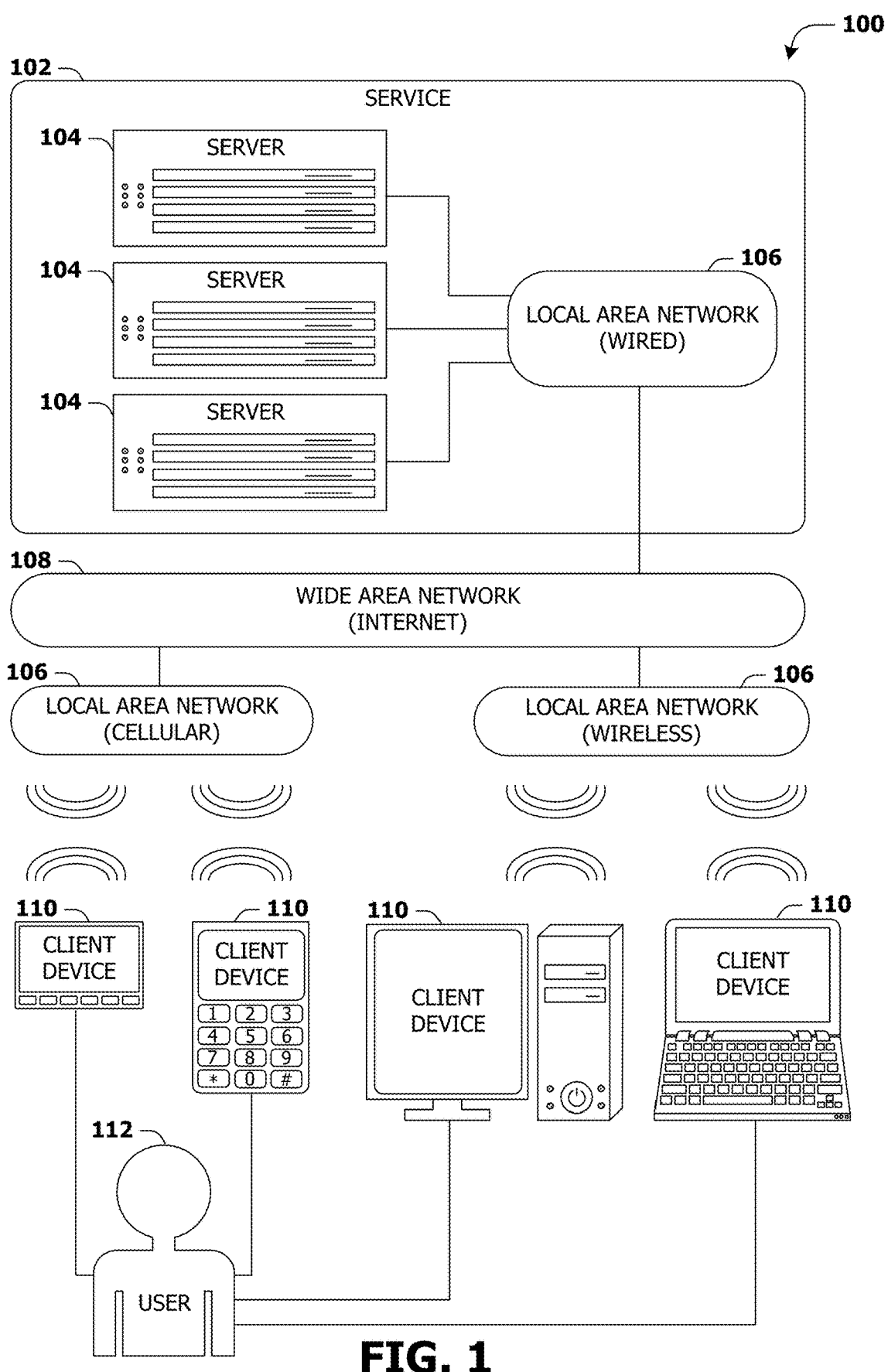
FIG. 1 is an illustration of a scenario involving various examples of networks that may connect servers and clients.

FIG. 1 is an interaction diagram of a scenario 100 illustrating a service 102 provided by a set of servers 104 to a set of client devices 110 via various types of networks. The servers 104 and/or client devices 110 may be capable of transmitting, receiving, processing, and/or storing many types of signals, such as in memory as physical memory states.

The servers 104 of the service 102 may be internally connected via a local area network 106 (LAN), such as a wired network where network adapters on the respective servers 104 are interconnected via cables (e.g., coaxial and/or fiber optic cabling), and may be connected in various topologies (e.g., buses, token rings, meshes, and/or trees).

The servers 104 may be interconnected directly, or through one or more other networking devices, such as routers, switches, and/or repeaters. The servers 104 may utilize a variety of physical networking protocols (e.g., Ethernet and/or Fiber Channel) and/or logical networking protocols (e.g., variants of an Internet Protocol (IP), a Transmission Control Protocol (TCP), and/or a User Datagram Protocol (UDP). The local area network 106 may include, e.g., analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. The local area network 106 may be organized according to one or more network architectures, such as server/client, peer-to-peer, and/or mesh architectures, and/or a variety of roles, such as administrative servers, authentication servers, security monitor servers, data stores for objects such as files and databases, business logic servers, time synchronization servers, and/or front-end servers providing a user-facing interface for the service 102.

Likewise, the local area network 106 may comprise one or more sub-networks, such as may employ differing architectures, may be compliant or compatible with differing protocols and/or may interoperate within the local area network 106. Additionally, a variety of local area networks 106 may be interconnected; e.g., a router may provide a link between otherwise separate and independent local area networks 106.

In the scenario 100 of FIG. 1, the local area network 106 of the service 102 is connected to a wide area network 108 (WAN) that allows the service 102 to exchange data with other services 102 and/or client devices 110. The wide area network 108 may encompass various combinations of devices with varying levels of distribution and exposure, such as a public wide-area network (e.g., the Internet) and/or a private network (e.g., a virtual private network (VPN) of a distributed enterprise).

In the scenario 100 of FIG. 1, the service 102 may be accessed via the wide area network 108 by a user 112 of one or more client devices 110, such as a portable media player (e.g., an electronic text reader, an audio device, or a portable gaming, exercise, or navigation device); a portable communication device (e.g., a camera, a phone, a wearable or a text chatting device); a workstation; and/or a laptop form factor computer. The respective client devices 110 may communicate with the service 102 via various connections to the wide area network 108. As a first such example, one or more client devices 110 may comprise a cellular communicator and may communicate with the service 102 by connecting to the wide area network 108 via a wireless local area network 106 provided by a cellular provider. As a second such example, one or more client devices 110 may communicate with the service 102 by connecting to the wide area network 108 via a wireless local area network 106 (and/or via a wired network) provided by a location such as the user's home or workplace (e.g., a WiFi (Institute of Electrical and Electronics Engineers (IEEE) Standard 802.11) network or a Bluetooth (IEEE Standard 802.15.1) personal area network). In this manner, the servers 104 and the client devices 110 may communicate over various types of networks. Other types of networks that may be accessed by the servers 104 and/or client devices 110 include mass storage, such as network attached storage (NAS), a storage area network (SAN), or other forms of computer or machine readable media.

1.2. Server Configuration

Figures 2, 3:
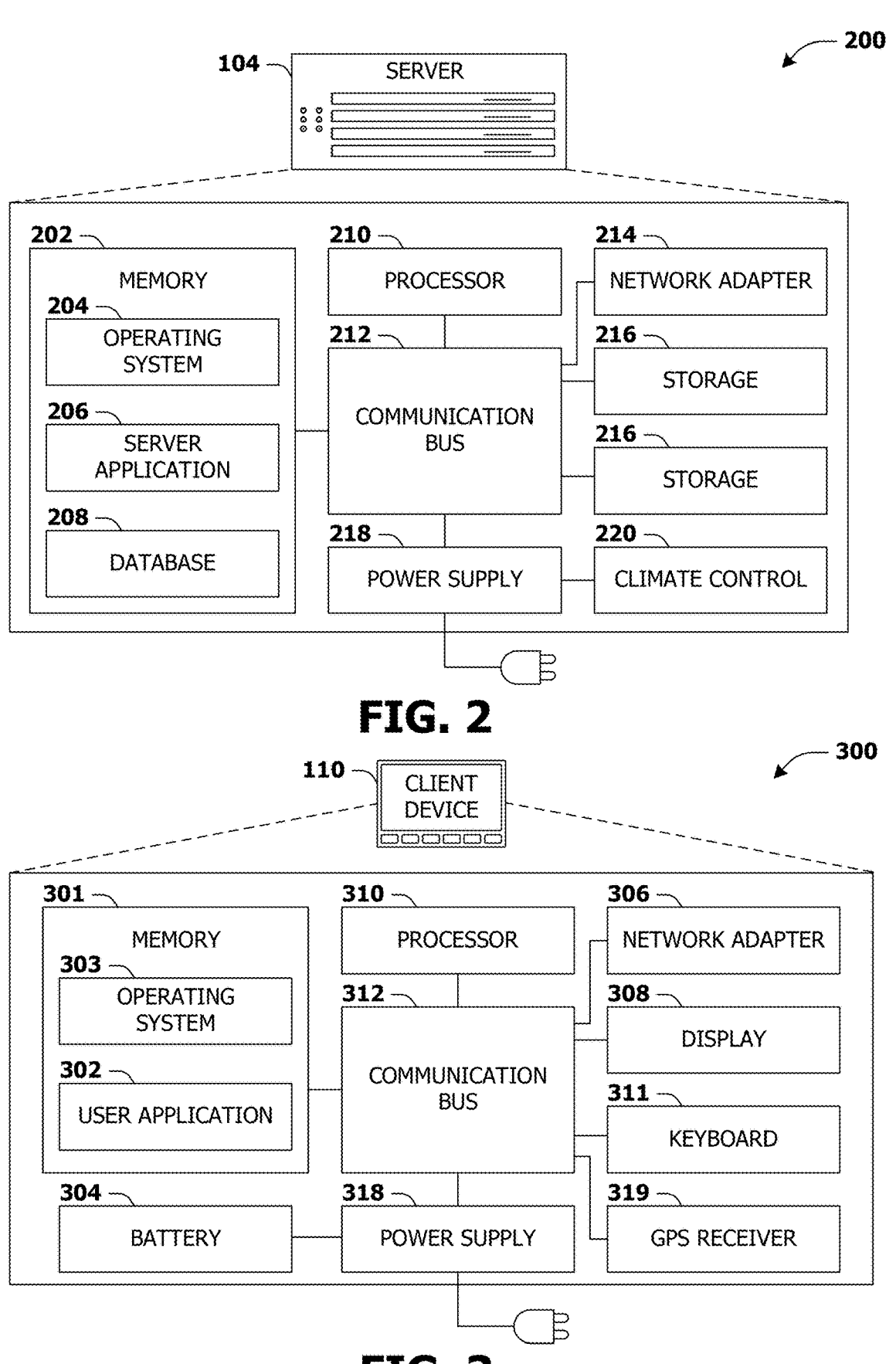
FIG. 2 is an illustration of a scenario involving an example configuration of a server that may utilize and/or implement at least a portion of the techniques presented herein.
FIG. 3 is an illustration of a scenario involving an example configuration of a client that may utilize and/or implement at least a portion of the techniques presented herein.

FIG. 2 presents a schematic architecture diagram 200 of a server 104 that may utilize at least a portion of the techniques provided herein. Such a server 104 may vary widely in configuration or capabilities, alone or in conjunction with other servers, in order to provide a service such as the service 102.

The server 104 may comprise one or more processors 210 that process instructions. The one or more processors 210 may optionally include a plurality of cores; one or more coprocessors, such as a mathematics coprocessor or an integrated graphical processing unit (GPU); and/or one or more layers of local cache memory. The server 104 may comprise memory 202 storing various forms of applications, such as an operating system 204; one or more server applications 206, such as a hypertext transport protocol (HTTP) server, a file transfer protocol (FTP) server, or a simple mail transport protocol (SMTP) server; and/or various forms of data, such as a database 208 or a file system. The server 104 may comprise a variety of peripheral components, such as a wired and/or wireless network adapter 214 connectible to a local area network and/or wide area network; one or more storage components 216, such as a hard disk drive, a solid-state storage device (SSD), a flash memory device, and/or a magnetic and/or optical disk reader.

The server 104 may comprise a mainboard featuring one or more communication buses 212 that interconnect the processor 210, the memory 202, and various peripherals, using a variety of bus technologies, such as a variant of a serial or parallel AT Attachment (ATA) bus protocol; a Uniform Serial Bus (USB) protocol; and/or Small Computer System Interface (SCI) bus protocol. In a multibus scenario, a communication bus 212 may interconnect the server 104 with at least one other server. Other components that may optionally be included with the server 104 (though not shown in the schematic diagram 200 of FIG. 2) include a display; a display adapter, such as a graphical processing unit (GPU); input peripherals, such as a keyboard and/or mouse; and a flash memory device that may store a basic input/output system (BIOS) routine that facilitates booting the server 104 to a state of readiness.

The server 104 may operate in various physical enclosures, such as a desktop or tower, and/or may be integrated with a display as an "all-in-one" device. The server 104 may be mounted horizontally and/or in a cabinet or rack, and/or may simply comprise an interconnected set of components. The server 104 may comprise a dedicated and/or shared power supply 218 that supplies and/or regulates power for the other components. The server 104 may provide power to and/or receive power from another server and/or other devices. The server 104 may comprise a shared and/or dedicated climate control unit 220 that regulates climate properties, such as temperature, humidity, and/or airflow. Many such servers 104 may be configured and/or adapted to utilize at least a portion of the techniques presented herein.

1.3. Client Device Configuration

FIG. 3 presents a schematic architecture diagram 300 of a client device 110 whereupon at least a portion of the techniques presented herein may be implemented. Such a client device 110 may vary widely in configuration or capabilities, in order to provide a variety of functionality to a user such as the user 112. The client device 110 may be provided in a variety of form factors, such as a desktop or tower workstation; an "all-in-one" device integrated with a display 308; a laptop, tablet, convertible tablet, or palmtop device; a wearable device mountable in a headset, eyeglass, earpiece, and/or wristwatch, and/or integrated with an article of clothing; and/or a component of a piece of furniture, such as a tabletop, and/or of another device, such as a vehicle or residence. The client device 110 may serve the user in a variety of roles, such as a workstation, kiosk, media player, gaming device, and/or appliance.

The client device 110 may comprise one or more processors 310 that process instructions. The one or more processors 310 may optionally include a plurality of cores; one or more coprocessors, such as a mathematics coprocessor or an integrated graphical processing unit (GPU); and/or one or more layers of local cache memory. The client device 110 may comprise memory 301 storing various forms of applications, such as an operating system 303; one or more user applications 302, such as document applications, media applications, file and/or data access applications, communication applications such as web browsers and/or email clients, utilities, and/or games; and/or drivers for various peripherals. The client device 110 may comprise a variety of peripheral components, such as a wired and/or wireless network adapter 306 connectible to a local area network and/or wide area network; one or more output components, such as a display 308 coupled with a display adapter (optionally including a graphical processing unit (GPU)), a sound adapter coupled with a speaker, and/or a printer; input devices for receiving input from the user, such as a keyboard 311, a mouse, a microphone, a camera, and/or a touch-sensitive component of the display 308; and/or environmental sensors, such as a global positioning system (GPS) receiver 319 that detects the location, velocity, and/or acceleration of the client device 110, a compass, accelerometer, and/or gyroscope that detects a physical orientation of the client device 110. Other components that may optionally be included with the client device 110 (though not shown in the schematic architecture diagram 300 of FIG. 3) include one or more storage components, such as a hard disk drive, a solid-state storage device (SSD), a flash memory device, and/or a magnetic and/or optical disk reader; and/or a flash memory device that may store a basic input/output system (BIOS) routine that facilitates booting the client device 110 to a state of readiness; and a climate control unit that regulates climate properties, such as temperature, humidity, and airflow.

The client device 110 may comprise a mainboard featuring one or more communication buses 312 that interconnect the processor 310, the memory 301, and various peripherals, using a variety of bus technologies, such as a variant of a serial or parallel AT Attachment (ATA) bus protocol; the Uniform Serial Bus (USB) protocol; and/or the Small Computer System Interface (SCI) bus protocol. The client device 110 may comprise a dedicated and/or shared power supply 318 that supplies and/or regulates power for other components, and/or a battery 304 that stores power for use while the client device 110 is not connected to a power source via the power supply 318. The client device 110 may provide power to and/or receive power from other client devices.

In some scenarios, as a user 112 interacts with a software application on a client device 110 (e.g., an instant messenger and/or electronic mail application), descriptive content in the form of signals or stored physical states within memory (e.g., an email address, instant messenger identifier, phone number, postal address, message content, date, and/or time) may be identified. Descriptive content may be stored, typically along with contextual content. For example, the source of a phone number (e.g., a communication received from another user via an instant messenger application) may be stored as contextual content associated with the phone number. Contextual content, therefore, may identify circum-stances surrounding receipt of a phone number (e.g., the date or time that the phone number was received), and may be associated with descriptive content. Contextual content, may, for example, be used to subsequently search for associated descriptive content. For example, a search for phone numbers received from specific individuals, received via an instant messenger application or at a given date or time, may be initiated. The client device 110 may include one or more servers that may locally serve the client device 110 and/or other client devices of the user 112 and/or other individuals. For example, a locally installed webserver may provide web content in response to locally submitted web requests. Many such client devices 110 may be configured and/or adapted to utilize at least a portion of the techniques presented herein.

2. Presented Techniques

A significant portion of the population leverages multiple virtual modalities to communicate. Such communication also happens across multiple geographic locations and participants represent diverse cultural backgrounds. As a result, steady & balanced communication behavior becomes vital for effective outcomes. However, there are times when users are in an emotional state (e.g., a mental state) which is not conducive to effectively regulate their behavior when they communicate with others. This is may be relevant to communication that occurs in both the personal and professional sphere of the user's life.

Thus, one or more computing devices and/or techniques for controlling a communication state based upon an emotional state of a user are provided. The present disclosure may provide a communication system (e.g., a machine learning based system) that integrates various vectors of input (e.g., metrics which may be available based upon permissions from the user and/or developer application programming interface (API) shared by an operating system) from wearable and/or other devices associated with the user (e.g., heart rate, temperature, rapidity of movement, voice intensity levels, etc.) to make predictions on the user's emotional state which in turn may be leveraged by the communication system make recommendations to the user and/or make adjustments to user interface behavior of a communication interface to optimize user behavior. The communication system may consume content associated with the user (e.g., the user's past messages across one or more channels associated with one or more communication platforms) to determine the type of messages the user usually creates when in a balanced state versus an aggravated state. Leveraging the inputs and insights, the communication system make predictions based on the user's vitals about the user's mental state to recommend actions when the user is in the process of communication. This may vary from suggesting more appropriate language to the user, to increasing the amount of time the user has to unsend the message and/or to suggesting the user avoid sending the message altogether until a later time. The communication system may recommend exercises to the user to return the user to a more balanced mental state.

Figure 4:
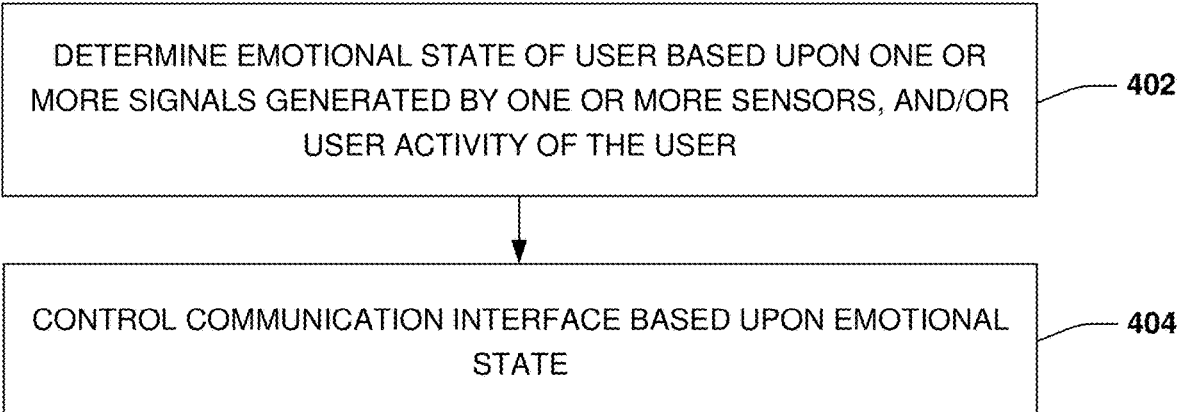
FIG. 4 is a flow chart illustrating an example method for controlling a communication interface based upon an emotional state of a user.

An embodiment of controlling a communication interface based upon an emotional state of a user is illustrated by an example method 400 of FIG. 4, and is further described in conjunction with a system 501 of FIGS. 5A-5J. In some examples, a communication system is provided. A user, such as user Jill, (and/or a first client device associated with the user) may access and/or interact with a service associated with the communication system. The service may comprise at least one of a browser, software, a website, an application, an operating system, an email interface, a messaging interface, a calling interface, a social network interface, etc. The service and/or the communication system may provide a communication platform for the user to at least one of (i) compose, send, receive and/or consume content (e.g., emails, text messages, instant messages, blog posts, social network posts, links, articles, videos, images, etc.) that are delivered to and/or received from one or more other users, (ii) post social network posts, (iii) view other users' social network posts, (iv) post a comment on a social network post on a social network, etc.

At 402, the communication system may determine an emotional state of the user based upon (i) a set of signals (e.g., a set of one or more signals) generated by a set of sensors (e.g., a set of one or more sensors) and/or (ii) user activity of the user. In some examples, the set of signals may comprise one or more biometric signals indicative of one or more biometric parameters (e.g., temperature, heart rate, etc.) associated with the user. For example, the set of signals comprise a temperature signal indicative of a temperature associated with the user (e.g., a body temperature associated with the user). The temperature signal may be generated using a temperature sensor of the set of sensors. The temperature sensor may be positioned proximal the user's body. In some examples, the temperature sensor may be disposed in a device (e.g., a wearable device) that is in contact with the user's body (e.g., the user's wrist).

In some examples, the set of signals may comprise a heart rate signal indicative of a heart rate associated with the user. The heart rate signal may be generated using a heart rate sensor of the set of sensors. The heart rate sensor may be positioned proximal the user's body. In some examples, the heart rate sensor may be disposed in a device (e.g., a wearable device) that is in contact with the user's body (e.g., the user's wrist).

In some examples, the set of signals may comprise an image signal indicative of an image (and/or video) captured by an image sensor (e.g., a camera) of the set of sensors. The image sensor may face the user and/or have a view of the user (e.g., a view of at least a portion of the user's face). In an example, the image sensor may comprise a camera embedded in a device (e.g., at least one of a laptop, tablet, smartphone, wearable device, etc. used by the user).

In some examples, the set of signals may comprise an audio signal indicative of audio captured by an audio sensor (e.g., a microphone) of the set of sensors. The audio sensor may within a distance of the user that allows the user's voice to be captured by the audio sensor. In an example, the image sensor may comprise a microphone embedded in a device (e.g., at least one of a laptop, tablet, smartphone, wearable device, etc. used by the user).

Figure 5A:
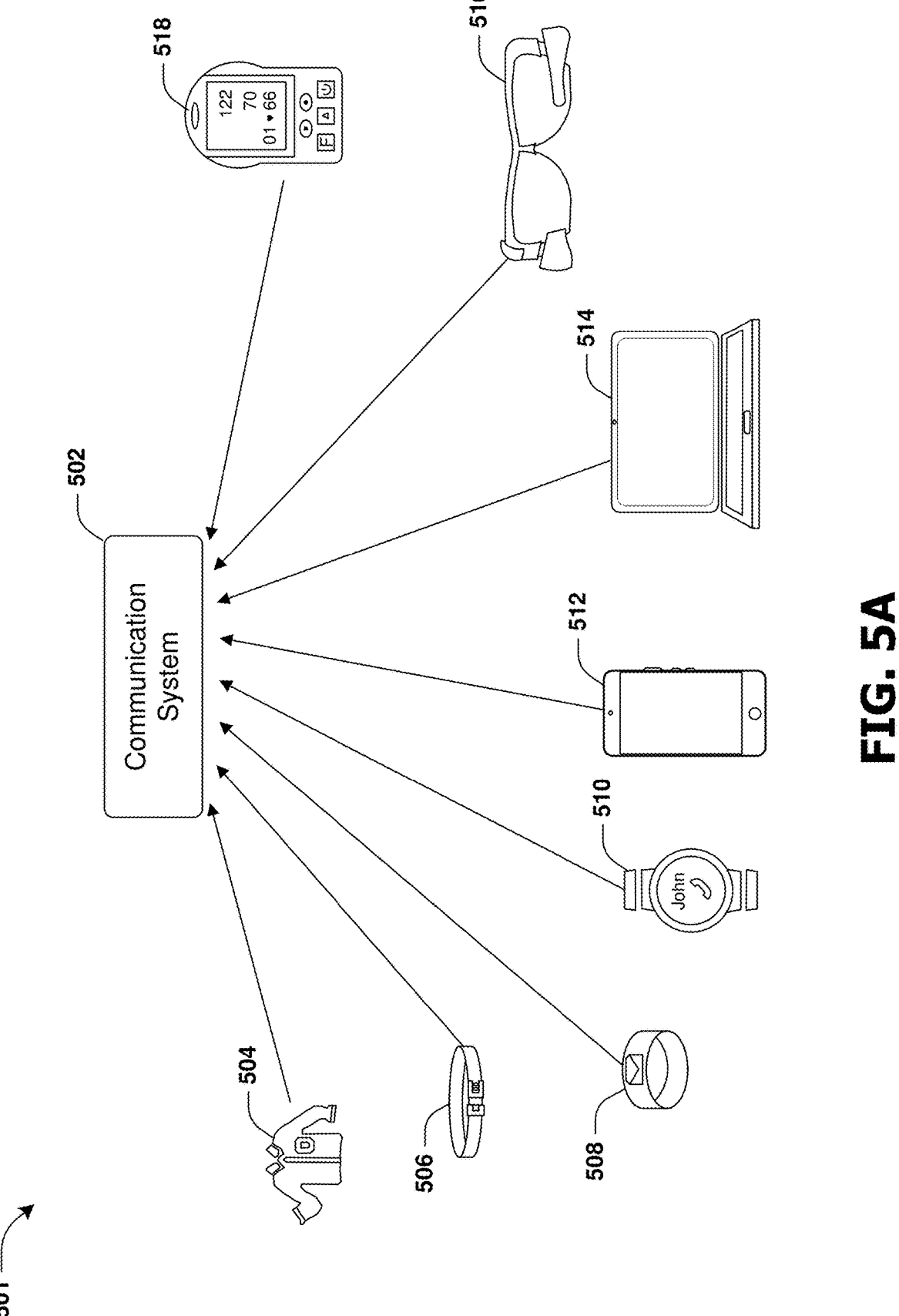
FIG. 5A is a component block diagram illustrating an example system for controlling a communication interface based upon an emotional state of a user, where a second communication interface is displayed via a first client device.

FIG. 5A illustrates reception of the set of signals from a set of client devices (e.g., a set of one or more client devices) associated with the user by the communication system (shown with reference number 502). In some examples, the set of client devices may comprise one or more devices (e.g., a smart ring 504, a smart belt 506, a smart ring 508, a smart watch 510, smart glasses 516, a healthcare device 518, etc.) each comprising (i) one or more sensors (e.g., a temperature sensor, a heart rate sensor, a blood pressure sensor, other type of biometric sensor, an image sensor, an audio sensor, etc.) and/or (ii) a transmitter for transmitting one or more signals (generated by the one or more sensors, for example) of the set of signals to the communication system 502 (e.g., the one or more signals may comprise at least one of temperature signal, heart rate signal, blood pressure signal, image signal, audio signal, etc.). In an example, the transmitter may transmit (via Bluetooth, Bluetooth Low Energy, WiFi, and/or other type of communication, for example) the one or more signals to an intermediate device. The intermediate device may transmit information (over the Internet, for example) indicative of the one or more signals to the communication system 502. In some examples, the set of client devices may comprise a smartphone 512 and/or a laptop 514. In some examples, one or more signals of the set of signals (e.g., at least one of temperature signal, heart rate signal, blood pressure signal, image signal, audio signal, etc.) may be generated using one or more sensors disposed in the smartphone 512 and/or the laptop 514, and/or the one or more signals may be transmitted to the communication system 502. In some examples, the intermediate device may comprise the smartphone 512 and/or the laptop 514 (and/or other device associated with the user).

In some examples, a first set of parameters (e.g., a set of one or more parameters) is determined based upon the set of signals. For example, the first set of parameters may comprise (i) the temperature (e.g., the body temperature), which may be determined based upon the temperature signal, (ii) the heart rate, which may be determined based upon the heart rate signal, (iii) a movement level (e.g., rapidity of movement, such as eye movement, of the user), which may be determined by analyzing the image signal and/or tracking motion of one or more features (e.g., eye, face, hand, other body part, etc.) of the user in a video provided by the image signal, (iv) a voice intensity level (e.g., how loud the user is speaking in units of decibels) associated with the user, which may be determined by analyzing the audio signal and/or measuring an intensity of the audio signal, (v) a facial expression of the user (e.g., anger facial expression, contempt facial expression, disgust facial expression, fear facial expression, tense facial expression, etc.), which may be determined by analyzing the image signal to determine the user's facial expression and/or tracking changes to the user's facial expression in a video provided by the image signal, (vi) a tension level associated with the user, (vii) a stress level associated with the user, and/or (viii) one or more other parameters.

In some examples, the user activity may include first user activity performed using a first communication interface (e.g., an email interface, a messaging interface, a calling interface, a social network interface, etc.). For example, the first user activity may comprise the user interacting with the first communication interface to at least one of compose, send, receive and/or consume content (e.g., emails, text messages, instant messages, blog posts, social network posts, links, articles, videos, images, etc.). For example, the user may interact with the first communication interface using the first client device (e.g., the smartphone 512, the laptop 514, and/or other device).

In an example, a graphical user interface of the first client device may be controlled to display the first communication interface. For example, the first communication interface may comprise a plurality of content items of a content items database associated with the first communication interface and/or a user account associated with the user and/or the first client device. In some examples, the plurality of content items and/or the content items database may comprise email items, message items, news items, video items, audio items, etc. Alternatively and/or additionally, the first communication interface may comprise a plurality of selectable inputs associated with transmitting items, deleting items, managing the user account, consuming items, etc. Alternatively and/or additionally, the first communication interface may comprise one or more text areas associated with composing messages and/or emails, editing and/or creating reports and/or social media posts, etc.

In some examples, the first user activity may comprise selectable inputs of the first communication interface being selected (e.g., clicked, pressed, etc.) using a touchscreen (e.g., of the first client device), one or more switches (e.g., one or more buttons), a conversational interface (e.g., a voice recognition and natural language interface), etc. For example, the selectable inputs may correspond to one or more content items of the plurality of content items, one or more settings associated with the user account, etc. Alternatively and/or additionally, the first user activity may comprise text being input into one or more text areas of the first communication interface. Alternatively and/or additionally, the first user activity may comprise one or more content items being consumed.

In an example, the first communication interface may be an email interface and/or the plurality of content items may comprise a plurality of emails. Accordingly, the first user activity may comprise one or more emails being selected, one or more emails being replied to, one or more emails being forwarded, one or more links within one or more emails being selected, one or more emails being composed, one or more emails being consumed, etc.

In some examples, the first user activity may include activity performed using the first communication interface during a first duration of time (e.g., 30 minutes, 1 hour, 1.5 hours, 3 hours, etc.). For example, the first user activity may be monitored and/or analyzed (periodically) throughout the first duration of time. In some example, the first user activity may include activity performed continuously. For example, (intermittent) periods of inactivity within the first duration of time may (each) be less than a first threshold duration of time (e.g., 5 minutes, 10 minutes, 20 minutes, etc.).

Alternatively and/or additionally, the first user activity may include activity performed using one or more interfaces different than the first communication interface. For example, the one or more interfaces and/or the first communication interface may be associated with a (single) system. Each content interface may be associated with a service, of a plurality of services, provided by the system. For example, the system may comprise an internet system providing a plurality of interfaces, where each interface of the plurality of interfaces may provide a service of the plurality of services (e.g., a search engine service, a news content service, a video platform service, an email interface, etc.). Alternatively and/or additionally, the system may comprise an operating system of the first client device.

Alternatively and/or additionally, the first user activity may include activity performed using one or more client devices, different than the first client device, associated with the user and/or the user account. For example, each client device of the one or more client devices may have the first communication interface installed (e.g., a version of the first communication interface associated with a client device of the one or more client devices may be installed on the client device). Alternatively and/or additionally, the first communication interface may be a web interface accessed via a browser of the client device and/or the one or more client devices.

In some examples, the text being input into the one or more text areas of the first communication interface may be monitored and/or analyzed. For example, an amount of the text may be determined. For example, the amount of the text may be indicative of a quantity of words of the text input into the one or more text areas, a quantity of characters (e.g., letters, symbols, spaces, etc.) of the text input into the one or more text areas, etc. Alternatively and/or additionally, a text-rate at which the text is input into the one or more text areas may be determined. For example, the text-rate may be indicative of a quantity of words input per unit of time (e.g., per minute, per hour, etc.), a quantity of words that are input continuously, a quantity of characters input per unit of time (e.g., per minute, per hour, etc.), etc.

Alternatively and/or additionally, an instrument used for inputting the text into the one or more text areas may be determined. For example, the instrument may be indicative of whether the text is input into the one or more text areas via typing using a keyboard associated with the first client device, whether the text is input into the one or more text areas via typing using an on-screen keyboard displayed using the touchscreen of the first client device, whether the text is input via the conversational interface of the first client device, etc.

Alternatively and/or additionally, a distance between key strokes associated with the text being input into the one or more text areas may be determined. For example, the distance between key strokes may be determined based upon the instrument used for inputting the text into the one or more text areas (e.g., whether the text is input via the keyboard and/or the on-screen keyboard). Alternatively and/or additionally, the distance between key strokes may be determined based upon a type of the keyboard (e.g., size of the keyboard, keyboard model of the keyboard, etc.) and/or a type of the on-screen keyboard (e.g., size of the on-screen keyboard, device model of the first client device, orientation (e.g., portrait, horizontal, etc.) associated with a display of the first client device, etc.). For example, characters of the text may be mapped to keys associated with the keyboard and/or the on-screen keyboard. Distances between sets of keys of the keys may be measured to determine the distance between key strokes. The distance between key strokes may be a cumulative distance (e.g., a total distance of a plurality of distances between key strokes associated with characters of the text) and/or the distance between key strokes may be an average distance (e.g., an average distance of the plurality of distances).

Alternatively and/or additionally, a key stroke effort associated with the text being input into the one or more text areas may be determined. For example, the key stroke effort may correspond to an amount of pressure needed to implement a key stroke (press a key). For example, the key stroke effort may be determined based upon the instrument used for inputting the text into the one or more text areas (e.g., whether the text is input via the keyboard and/or the on-screen keyboard). Alternatively and/or additionally, the key stroke effort may be determined based upon the type of the keyboard (e.g., the keyboard model), settings associated with the keyboard, the type of the on-screen keyboard and/or settings associated with the on-screen keyboard.

Alternatively and/or additionally, a writing effort associated with the text being input into the one or more text areas may be determined. For example, the writing effort may correspond to an amount of effort (e.g., mental effort, cognitive load, etc.) it may take for the user to develop and/or create the text. For example, the writing effort may be determined by analyzing content (e.g., words, sentences, subject matter, etc.) of the text and/or determining a level of complexity of the content (based upon the words, sentence structure, subject matter, etc. of the text). For example, in an instance where the text comprises complex descriptions of ideas and/or entities, the level of complexity and/or the writing effort may be determined to be higher than an instance where the text merely comprises simple descriptions (e.g., an address of a location, a phone number, etc.).

In some examples, a measure of writing activity may be generated based upon the text input into the one or more areas of the first communication interface. For example, the measure of writing activity may be generated based upon the amount of the text, the text-rate at which the text is input into the one or more text areas, the instrument used for inputting the text into the one or more text areas, the distance between key strokes, the key stroke effort and/or the writing effort. For example, the measure of writing activity may be generated by combining two or more of the amount of the text, the text-rate at which the text is input into the one or more text areas, the instrument used for inputting the text into the one or more text areas, the distance between key strokes, the key stroke effort and/or the writing effort.

In some examples, first selections of selectable inputs of the first communication interface may be monitored and/or analyzed. For example, an amount of the first selections of the selectable inputs may be determined. For example, the amount of the first selections may be indicative of a quantity of selections of selectable inputs of the first communication interface. Alternatively and/or additionally, a selection-rate at which selections of the first selections are performed may be determined. For example, the selection-rate may be indicative of a quantity of selections performed per unit of time (e.g., per minute, per hour, etc.), etc.

Alternatively and/or additionally, a second instrument used for performing the first selections may be determined. For example, the second instrument may be indicative of whether the first selections are performed using the touch-screen of the first client device, the conversational interface of the first client device, the keyboard associated with the first client device, a mouse associated with the first client device, a remote control (e.g., a wireless remote control) associated with the first client device, etc.

Alternatively and/or additionally, a number of steps associated with selections of the first selections may be determined. For example, it may be necessary to select more than one selectable input in order to perform a first selection of a first selectable input (e.g., the first selection of the first selectable input may involve two or more steps). In the example where the first communication interface is an email interface, the first selectable input may correspond to forwarding an email. In some examples, before selecting the first selectable input (and/or forwarding the email), a second selectable input corresponding to the email must be selected (to open the email). For example, responsive to a selection of the second selectable input, a page comprising the email and/or the first selectable input may be displayed. The first selectable input may be selected via the page.

Alternatively and/or additionally, a selection effort associated with the first selections may be determined. The selection effort may correspond to an amount of effort (e.g., mental effort, cognitive load, etc.) it may take for the user to perform selections of the first selections. For example, an amount of effort associated with first types of selections (e.g., selections associated with displaying content items, selections associated with logging into the user account, etc.) may be less than an amount of effort associated with second types of selections (e.g., selections associated with completing a transfer of funds, selections associated with organizing content items, selections associated with requesting transmission of emails and/or messages to important contacts, such as clients, etc.).

In some examples, a measure of selecting activity may be generated based upon the first selections of selectable inputs of the first communication interface. For example, the measure of selecting activity may be generated based upon the amount of the first selections, the selection-rate at which selections of the first selections are performed, the second instrument used for performing the first selections, the number of steps associated with selections of the first selections and/or the selection effort associated with the first selections. For example, the measure of selecting activity may be generated by combining two or more of the amount of the first selections, the selection-rate at which selections of the first selections are performed, the second instrument used for performing the first selections, the number of steps associated with selections of the first selections and/or the selection effort associated with the first selections.

Alternatively and/or additionally, consuming activity associated with a set of content items (e.g., a set of one or more content items) of the plurality of content items being consumed may be monitored and/or analyzed. In some examples, it may be determined that a content item of the plurality of content items is being consumed based upon interactions with the content item (e.g., selecting sets of text of the content item, scrolling through portions of the content item, pressing pause and/or play, etc.), a duration of time that the content item is displayed, etc. For example, an amount of content associated with the set of content items may be determined. For example, the amount of content may be indicative of a quantity of words of the set of content items, a quantity of characters of the set of content items, a time-length of one or more videos of the set of content items consumed, etc. Alternatively and/or additionally, the amount of content may be indicative of a second duration of time that the set of content items are consumed (e.g., the second duration of time that the user spends consuming the set of content items).

Alternatively and/or additionally, a consume-rate at which content items of the set of content items are consumed may be determined. For example, the consume-rate may be indicative of a quantity of words consumed per unit of time (e.g., per minute, per hour, etc.), a quantity of images consumed per unit of time (e.g., per minute, per hour, etc.), a quantity of content items consumed per unit of time (e.g., per minute, per hour, etc.), etc.

Alternatively and/or additionally, a third instrument used for consuming the set of content items may be determined. For example, the third instrument may be indicative of a size of the display of the first client device (e.g., consuming the set of content items using a smaller display may be more difficult than consuming the set of content items using a larger display). Alternatively and/or additionally, a consuming effort associated with the set of content items being consumed may be determined. For example, the consuming effort may correspond to an amount of effort (e.g., mental effort, cognitive load, etc.) it may take for the user to consume (e.g., read, view, listen to, comprehend, learn, etc.) the set of content items. For example, the consuming effort may be determined by analyzing content (e.g., words, sentences, subject matter, etc.) of the set of content items and/or determining a second level of complexity of the set of content items.

In some examples, a measure of consuming activity may be generated based upon the consuming activity associated with the set of content items being consumed. For example, the measure of consuming activity may be generated based upon the amount of content associated with the set of content items, the consume-rate at which content items of the set of content items are consumed, the third instrument used for consuming the set of content items and/or the consuming effort associated with set of content items being consumed. For example, the measure of consuming activity may be generated by combining two or more of the amount of content associated with the set of content items, the consume-rate at which content items of the set of content items are consumed, the third instrument used for consuming the set of content items and/or the consuming effort associated with set of content items being consumed.

In some examples, a plurality of requests received from the first client device may be monitored and/or analyzed. In some examples, a first quantity of requests of the plurality of requests associated with the first user activity may be determined. For example, the plurality of requests may be received from the first client device while the first user activity is being performed. For example, the plurality of requests may comprise authentication requests, requests for content, application programming interface (API) requests (e.g., API calls), requests to access resources, requests for transmission of messages and/or emails, etc.

Alternatively and/or additionally, a request-rate at which requests of the plurality of requests are received from the first client device may be determined. For example, the request-rate may be indicative of a quantity of requests received from the first client device per unit of time (e.g., per minute, per hour, etc.), etc. In some examples, a measure of requesting activity may be generated based upon the plurality of requests received from the first client device. For example, the measure of requesting activity may be generated based upon the quantity of requests of the plurality of requests and/or the request-rate at which requests of the plurality of requests are received. Alternatively and/or additionally, the measure of requesting activity may be generated by combining the quantity of requests of the plurality of requests and the request-rate at which requests of the plurality of requests are received.

In some examples, the plurality of requests may be used to determine content items that are consumed, emails and/or messages that are transmitted, the text that is input into the one or more text areas, etc. In some examples, a plurality of transmissions of items associated with the first user activity may be monitored and/or analyzed. For example, a quantity of transmissions of items (e.g., items may be emails, messages, instant messages, blog posts, social media posts, files etc.) of the plurality of transmissions of items (e.g., items may be transmitted to contacts, posted on blogs, posted on social media, etc.) may be determined. Alternatively and/or additionally, a transmission-rate at which items are transmitted may be determined. The transmission-rate may be indicative of a quantity of items transmitted per unit of time (e.g., per minute, per hour, etc.) (e.g., a quantity of transmissions per unit of time), etc.

In some examples, a measure of transmission activity may be generated based upon the quantity of transmissions of items of the plurality of transmissions of items and/or the transmission-rate at which items are transmitted. Alternatively and/or additionally, the measure of transmission activity may be generated by combining the quantity of transmissions of items of the plurality of transmissions of items and the transmission-rate at which items are transmitted.

A first level of activity associated with the user may be determined based upon the first user activity. In some examples, the first level of activity may be generated based upon the measure of writing activity, the measure of selecting activity, the measure of consuming activity, the measure of requesting activity and/or the measure of transmission activity. Alternatively and/or additionally, the first level of activity may be generated by combining two or more of the measure of writing activity, the measure of selecting activity, the measure of consuming activity, the measure of requesting activity and/or the measure of transmission activity.

For example, a first set of representations (e.g., a set of one or more representations, such as a set of one or more vector representations) may be generated based upon the measure of writing activity. A second set of representations may be generated based upon the measure of selecting activity. A third set of representations may be generated based upon the measure of consuming activity. A fourth set of representations may be generated based upon the measure of requesting activity. A fifth set of representations may be generated based upon the measure of transmission activity. Two or more sets of representations of the first set of representations, the second set of representations, the third set of representations, the fourth set of representations and/or the fifth set of representations may be combined to generate the first level of activity.

In some examples, the communication system 502 may evaluate first content associated with the user activity to determine a first classification (e.g., an explicit classification) of the first content. In some examples, the communication system 502 may generate the first classification (to classify the first content). Alternatively and/or additionally, the communication system 502 may select the first classification from a plurality of classifications (e.g., a predefined list of classifications) comprising at least one of an anger classification, a flowery classification, a racist classification, a controversial topic classification, a hurtful classification, a slanderous classification, a sexist classification, an inappropriate classification, a negative interpretation classification, an out of context classification, a communication to boss classification (for a communication, such as an email and/or a text message, to the user's boss, for example), a communication to wife classification, and/or a variety of other classifications.

In some examples, the first content comprises at least one of text, one or more images, one or more videos, audio, a social media post, a comment on a social media post, etc. In some examples, the first content is generated and/or identified (and/or consumed) by the user. In an example, the first content may comprise the text that was input into the one or more text areas. Alternatively and/or additionally, the first content may comprise an email, a text message, a social network message, a social network post, a video post, an image, a social network comment on a post, a video call, a voice call, a link to external content and/or other type of content. In some examples, the first content comprises at least a portion of a content item (e.g., text, one or more images, one or more videos, audio, a social media post, a comment on a social media post, etc.) of the set of content items consumed by the user.

In an example, the first content may comprise a message, a post, or other content comprising content items that the user did (e.g., text created by the user) or did not generate (e.g., an image that the user found and is sharing through a social network post). Thus, one or more content items within the first content may be evaluated for classifying the first content. The first content may be evaluated and/or classified as the first classification before the user has submitted the first content for access by other users, such as before an email has been sent or a social network post has been posted. Various classification techniques may be used to classify the first content, such as machine learning (e.g., Naïve Bayes), image recognition, a text parser and classifier, entity extraction, audio and voice recognition, a feature extractor, and/or a variety of other techniques that can classify content and content items comprised therein.

In some examples, the communication system 502 may evaluate second content associated with the user activity to determine a first sentiment of the second content. In some examples, the second content comprises at least one of text, one or more images, one or more videos, audio, a social media post, a comment on a social media post, etc. In some examples, the second content is generated and/or identified (and/or consumed) by the user. In an example, the second content may comprise the text that was input into the one or more text areas. Alternatively and/or additionally, the second content may comprise an email, a text message, a social network message, a social network post, a video post, an image, a social network comment on a post, a video call, a voice call, a link to external content and/or other type of content. In some examples, the second content comprises at least a portion of a content item (e.g., text, one or more images, one or more videos, audio, a social media post, a comment on a social media post, etc.) of the set of content items consumed by the user. In some examples, the second content is different than the first content. Embodiments are contemplated in which the second content is the same as the first content (e.g., the first sentiment and the first classification are both determined based upon the same content).

In an example, the second content may comprise a message, a post, or other content comprising content items that the user did or did not generate. In an example in which the second content is at least one of a message, an email, a social media post, etc. (created by the user, for example) that is not yet submitted for access by other users, the second content may be evaluated to determine the first sentiment before the user has submitted the second content for access by other users, such as before the email or the message has been sent or the social network post has been posted.

A sentiment of a content item (e.g., the first sentiment of the second content) may correspond to subjective information, such as emotions, opinions, feelings, thoughts, facts, judgments and/or assessments that are expressed by the content item. Alternatively and/or additionally, the sentiment of the content item may correspond to emotions, opinions, feelings, thoughts, facts, judgments and/or assessments that a user who consumed the content item may have. Alternatively and/or additionally, the sentiment of the content item may correspond to a sentiment category. The sentiment category may be indicative of an intensity of emotions, opinions, feelings, thoughts, facts, judgments and/or assessments. For example, the sentiment category may be indicative of a level of positivity of the content item towards (and/or about) one or more entities (e.g., one or more people, one or more organizations, one or more events, one or more ideas, etc.) associated with the content item (e.g., a level of favorability of feelings, thoughts, judgments and/or assessments associated with the content item and/or a user who consumed the content item towards the one or more entities) and/or a level of negativity of the content item towards (and/or about) one or more entities (e.g., a level unfavorability of feelings, thoughts, judgments and/or assessments associated with the content item and/or a user who consumed the content item towards the one or more entities).

In an example, a first positive sentiment category may be indicative of a first level of positivity (and/or a first range of levels of positivity), a second positive sentiment category may be indicative of a second level of positivity (and/or a second range of levels of positivity), etc. Alternatively and/or additionally, a first negative sentiment category may be indicative of a first level of negativity (and/or a first range of levels of negativity), a second negative sentiment category may be indicative of a second level of negativity (and/or a second range of levels of negativity), etc.

Alternatively and/or additionally, the sentiment category may be indicative of a polarity of emotions, opinions, feelings, thoughts, facts, judgments and/or assessments. For example, a first sentiment category may be indicative of the content item expressing negative (and/or unfavorable) emotions, opinions, feelings, thoughts, facts, judgments and/or assessments and/or a user who consumed the content item having negative emotions, opinions, feelings, thoughts, facts, judgments and/or assessments based upon the content item. Alternatively and/or additionally, a second sentiment category may be indicative of the content item expressing positive emotions, opinions, feelings, thoughts, facts, judgments and/or assessments and/or a user who consumed the content item having positive emotions, opinions, feelings, thoughts, facts, judgments and/or assessments based upon the content item. Alternatively and/or additionally, a third sentiment category may be indicative of the content item expressing neutral emotions, opinions, feelings, thoughts, facts, judgments and/or assessments and/or a user who consumed the content item having neutral emotions, opinions, feelings, thoughts, facts, judgments and/or assessments based upon the content item.

In some examples, the communication system 502 may determine the emotional state of the user based upon the set of parameters, the first level of activity, the first classification and/or the first sentiment. In some examples, the communication system 502 selects the emotional state from a plurality of emotional states comprising at least one of angry, sad, balanced, aggravated, agitated, tense, stressed, tired, exhausted, light-headed, happy, fearful, surprised, disgusted, happily surprised, happily disgusted, sadly fearful, sadly angry, sadly surprised, sadly disgusted, fearfully angry, fearfully surprised, fearfully disgusted, angrily surprised, angrily disgusted, disgustedly surprised, appalled, hatred, awed, etc.

In an example, the communication system 502 may determine the emotional state of the user to be a first emotional state (e.g., angry, sad, aggravated, agitated, tense, stressed, tired, exhausted, hatred, etc.) based upon at least one of (i) the temperature (e.g., the body temperature) meeting (e.g., exceeding or being less than) a first threshold temperature or being within a first defined range of temperatures, (ii) the heart rate meeting (e.g., exceeding or being less than) a first threshold heart rate or being within a first defined range of heart rates, (iii) the movement level (e.g., rapidity of eye movement of the user) meeting (e.g., exceeding or being less than) a first threshold movement level or being within a first defined range of movement levels, (iv) the voice intensity level meeting (e.g., exceeding or being less than) a first threshold voice intensity level or being within a first defined range of voice intensity levels, (v) the tension level meeting (e.g., exceeding or being less than) a first threshold tension level or being within a first defined range of tension levels, (vi) the stress level meeting (e.g., exceeding or being less than) a first threshold stress level or being within a first defined range of stress levels, (vii) the first level of activity meeting (e.g., exceeding or being less than) a first threshold level of activity or being within a first defined range of levels of activity, (viii) the first classification being within a first set of classifications associated with the first emotional state, (ix) the first sentiment of the second content being indicative of the first sentiment category (e.g., negative sentiment), (x) one or more parameters (e.g., the temperature and/or the heart rate) fluctuating (by more than a threshold level of fluctuation, for example), and/or (xi) one or more other parameters meeting one or more other conditions.

In an example, the communication system 502 may determine the emotional state of the user to be a second emotional state (e.g., balanced, happy, etc.) based upon at least one of (i) the temperature (e.g., the body temperature) meeting (e.g., exceeding or being less than) a second threshold temperature or being within a second defined range of temperatures, (ii) the heart rate meeting (e.g., exceeding or being less than) a second threshold heart rate or being within a second defined range of heart rates, (iii) the movement level (e.g., rapidity of eye movement of the user) meeting (e.g., exceeding or being less than) a second threshold movement level or being within a second defined range of movement levels, (iv) the voice intensity level meeting (e.g., exceeding or being less than) a second threshold voice intensity level or being within a second defined range of voice intensity levels, (v) the tension level meeting (e.g., exceeding or being less than) a second threshold tension level or being within a second defined range of tension levels, (vi) the stress level meeting (e.g., exceeding or being less than) a second threshold stress level or being within a second defined range of stress levels, (vii) the first classifi-cation being part of a second set of classifications that are associated with the second emotional state, (vi) the stress level meeting (e.g., exceeding or being less than) a second threshold stress level or being within a second defined range of stress levels, (vii) the first level of activity meeting (e.g., exceeding or being less than) a second threshold level of activity or being within a second defined range of levels of activity, (viii) the first classification being within a second set of classifications associated with the second emotional state, (ix) the first sentiment of the second content being indicative of the second sentiment category (e.g., positive sentiment), and/or (x) one or more other parameters meeting one or more other conditions.

In some examples, the communication system 502 may determine the emotional state using a trained emotional state prediction model. In some examples, the communication system 502 may train a machine learning model to generate the trained emotional state prediction model using a set of training information. The set of training information may comprise (i) one or more historical emotional states associ-ated with the user, (ii) historical user activity associated with the user, (iii) historical parameters (e.g., one, some or all of the set of parameters) associated with the user (iv) historical classifications of content associated with the user (e.g., the first classification of the first content and/or other classifi-cations of other content generated and/or consumed by the user), and/or (v) historical sentiments of content associated with the user (e.g., the first sentiment of the second content and/or other sentiments of other content generated and/or consumed by the user). In some examples, the one or more historical emotional states may be determined based upon feedback received from the user in a training phase of the trained emotional state prediction model. For example, the first client device may be controlled to display an emotional state tracking interface that provides the user with an option to provide an indication of the user's emotional state (e.g., the user may be presented with a list of emotional state identifiers from which the user can select one that best fits how the user is feeling), which may be included in the set of training information to train and/or test the trained emotional state prediction model. In some examples, the historical parameters may comprise (and/or may be based upon)

historical sensor-based information (e.g., the set of signals) generated using one or more sensors of the set of sensors.

At 404, the communication system 502 may control a second communication interface based upon the emotional state of the user. In some examples, the second communi-cation interface is the same as the first communication interface. Alternatively and/or additionally, the second com-munication interface may be different than the first commu-nication interface. In an example, the first communication interface may correspond to a web application accessed by the user via a first type of client device (e.g., a desktop, laptop, tablet and/or smartphone with a browser) and/or the second communication interface may correspond to a mobile application accessed by the user via a second type of client device (e.g., the mobile application may be installed on a smartphone associated with the user). In some examples, the communication system 502 may control a plurality of interfaces (e.g., the first communication inter-face, the second communication interface, etc. and/or one or more other interfaces for consuming and/or sharing content such as at least one of text, videos, images, audio, blogs, articles, etc.) associated with the user using one or more of the techniques provided herein.

In some examples, the communication system 502 may evaluate the emotional state of the user and/or the first classification to determine whether there is a first conflict between the emotional state and the first classification. In some examples, the first conflict may be identified when a combination of the first classification and the emotional state of the user is deemed to potentially result in one or more negative consequences (e.g., at least one of job loss, shame, annoyance, or hurt feelings) if the first content (i) was consumed by the user having the emotional state and/or (ii) was sent to one or more other users. In some examples, the first conflict may be identified based upon a set of classifi-cation-emotional state pairs that indicate conflict and/or potentially result in negative consequences. In some examples, the set of classification-emotional state pairs may comprise (i) a first classification-emotional state pair com-prising a combination of a classification indicating that corresponding content is an email from the user's boss and the emotional state of the user indicating that the user is exhausted and/or light-headed, (ii) a second classification-emotional state pair comprising a combination of a classi-fication indicating that corresponding content is an email to the user's boss and the emotional state of the user indicating that the user is angry, and/or (iii) one or more other classi-fication-emotional state pairs.

In an example, the first conflict may correspond to a conflict between (i) the first classification indicating that the first content is an email from the user's boss and/or indi-cating that the first content includes complex information that requires a significant level of consuming effort (e.g., mental effort, cognitive load, etc.) for the user to consume and/or (ii) the emotional state of the user indicating that the user is exhausted and/or light-headed. The first conflict may be associated with a negative consequence of the user not sufficiently understanding at least a portion of the email of the first content in their exhausted and/or light-headed state, which may result in the user not managing their job respon-sibilities (and/or other responsibilities) appropriately. For example, the communication system 502 may compare the first classification and/or the emotional state with one or more classification-emotional state pairs of the set of clas-sification-emotional state pairs, and/or may identify the first conflict based upon a determination that the first classification-emotional state pair matches (e.g., is similar to and/or at least partially equal to) the first classification and/or the emotional state.

In an example, the first conflict may correspond to a conflict between (i) the first classification indicating that the first content is an email to the user's boss and/or (ii) the emotional state of the user indicating that the user is angry. The first conflict may be associated with a negative consequence of the user potentially sending a rude and/or abnormal email in their angry state, which may result in the user offending, annoying and/or upsetting the boss. For example, the communication system 502 may compare the first classification and/or the emotional state with one or more classification-emotional state pairs of the set of classification-emotional state pairs, and/or may identify the first conflict based upon a determination that the second classification-emotional state pair matches (e.g., is similar to and/or at least partially equal to) the first classification and/or the emotional state.

In some examples, the communication system 502 may control the second communication interface based upon the first classification of the first content and/or the first sentiment of the second content. In an example, the communication system 502 may use the emotional state of the user, the first classification of the first content and/or the first sentiment of the second content to perform one or more adaptive actions associated with controlling the second communication interface (and/or adapting the second communication interface based upon the emotional state of the user and/or changes to the emotional state of the user), such as (i) generate and/or display one or more representations of replacement content, (ii) generate and/or display one or more representations of one or more recommended actions, (iii) generate and/or display a user interface populated with an activity for the user to perform, (iv) identify one or more problematic sections of content, and/or (v) adapt (e.g., automatically and/or dynamically adapt) user interface behavior of the second communication interface (e.g., adjust unsend duration of time associated with the second communication interface).

The one or more adaptive actions may be performed in response to identifying the first conflict associated with the first classification and/or the emotional state. Alternatively and/or additionally, the communication system 502 may maintain (i) a set of triggering emotional states that will trigger the implementation of the one or more adaptive actions, (ii) a set of triggering classifications that will trigger the implementation of the one or more adaptive actions, and/or (iii) a set of triggering sentiments that will trigger the implementation of the one or more adaptive actions. The one or more adaptive actions may be performed in response to (i) determining that the emotional state of the user matches an emotional state of the set of triggering emotional states, (ii) determining that the first classification matches a classification of the set of triggering classifications, and/or (iii) determining that the first sentiment matches a sentiment of the set of triggering sentiments.

The set of triggering emotional states may comprise angry, sad, aggravated, agitated, tense, stressed, tired, exhausted, hatred, and/or a variety of other emotional states. The set of triggering classifications may comprise an anger classification, a flowery classification, a racist classification, a controversial topic classification, a hurtful classification, a slanderous classification, a sexist classification, an inappropriate classification, a negative interpretation classification (e.g., a message that could be easily misinterpreted in a negative manner), an out of context classification (e.g., a message that could be easily taken out of context), and/or a variety of other classifications. The set of triggering sentiments may comprise the first negative sentiment category, the second negative sentiment category and/or other sentiment category.

In some examples, the communication system 502 may use a generative artificial intelligence (AI) tool to generate replacement content based upon the emotional state, the first classification and/or the first sentiment. In some examples, the generative AI tool may comprise a language model, such as large language model (LLM).

In some examples, the generative AI tool generates the replacement content based upon a first prompt (e.g., a set of guidance information) input to the generative AI tool. The first prompt may comprise (i) an input set of content (e.g., at least a portion of the first content, the second content and/or other content associated with the user) (ii) an indication of the first classification associated with the input set of content, (iii) an indication of the first sentiment associated with the input set of content, (iv) an indication of the emotional state of the user and/or (v) instructions (e.g., chain-of-thought (COT) instructions) based upon which the generative AI tool may generate the replacement content. In an example, the first prompt may comprise an instruction to rephrase the input set of content to generate the replacement content. In an example, the first prompt may comprise an instruction to shorten or lengthen the input set of content to generate the replacement content. In some examples, the first prompt may comprise an instruction to generate the replacement content to not have a negative characteristic. The negative characteristic may be based upon the first classification and/or the first sentiment. In an example in which the first classification indicates that the input set of content includes "annoying" content and/or the first sentiment indicates that the input set of content includes "negative" content, the first prompt may comprise an instruction to generate content, that could potentially replace at least some of the input set of content, that is not annoying and/or is not negative.

In some examples, the generative AI tool comprises one or more machine learning models (e.g., generative machine learning models). In some examples, the one or more machine learning models may comprise one or more generative pre-trained transformer models. In some examples, the one or more machine learning models may comprise one or more text generation models (to generate text of the replacement content, for example).

In some examples, the generative AI tool may be trained (e.g., pre-trained) and/or fine-tuned using one or more datasets (e.g., a knowledge base for generating text) to enable the generative AI tool to understand language context and/or generate text. The one or more datasets may comprise at least one of a corpus, such as a text corpus, one or more dictionaries, one or more lists of terms, one or more encyclopedias, one or more online encyclopedias, one or more news channel resources, one or more news websites, one or more websites, one or more books, one or more research articles, one or more research article databases, one or more informational databases, etc.) and/or other resources, which may enable the generative AI tool to develop a deep understanding of language context, thereby enabling the communication system to comprehend the input set of content more accurately and/or leading to better results associated with generation the replacement content.

In some examples, the communication system 502 may display a representation of the replacement content (via the second communication interface, for example). Alternatively and/or additionally, the communication system 502 may provide (via the second communication interface, for example) the user with an option to replace the input set of content with the replacement content. In some examples, the communication system 502 may generate the replacement content, display a representation of the replacement content and/or provide the user with the option to replace the input set of content with the replacement content in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments.

In some examples, the communication system 502 may determine a set of recommended actions (e.g., a set of one or more recommended actions) based upon the emotional state, the first classification and/or the first sentiment. In some examples, the set of recommended actions may comprise (i) postponing consumption of content, (ii) postponing transmission of the content to one or more other users, (iii) rephrasing the content (iv) a relaxing action, (v) muting an ongoing call (e.g., audio and/or video call between the user and one or more other users), (vi) leaving (e.g., disconnecting from) the ongoing call, (vii) rejoining the ongoing call at a later time (e.g., after five minutes or other duration for the user to rest, gather their thoughts and/or calm down) and/or (viii) one or more other actions. In an example, the ongoing call may comprise at least one of a telephone call, a Voice over Internet Protocol (VoIP) call, or other type of call. In some examples, the communication system 502 may display a representation of the set of recommended actions (via the second communication interface, for example). In some examples, the communication system 502 may determine the set of recommended actions and/or display a representation of the set of recommended actions in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments.

In some examples, the communication system 502 may generate a user interface to comprise an activity and/or instructions of the activity and/or may display the user interface (via the second communication interface, for example) in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments. In some examples, the activity may comprise a puzzle, a game, a math problem, an article to read and/or answer questions about, a cool off period (e.g., timeout period), a video to watch and/or answer questions about, a question and answer session, a suggested activity (e.g., count to ten, take a walk, etc.), a mental exercise to help the user return to a more balanced state (which may allow the user to reconsider any negative consequences, for example), etc. In some examples, the user may be restricted from performing a first action (e.g., submitting content for access by other users, consuming and/or viewing content, etc.) until the user successfully performs the activity. If the user successfully performs the activity, then the user may be provided with an option to perform the first action. In an example in which the activity comprises the cool off period, the user may be instructed to wait for the cool off period before being able to initiate the first action.

In an example, such as in a scenario in which there is content (e.g., the first content and/or the second content), such as at least one of a message, an email, a social media post, etc. (created by the user, for example), that is not yet submitted for access by other users, the user may be restricted from performing the first action (e.g., submitting the content for access by other users) until successful performance of the activity. In an example, the user may be provided with an override option that will allow the user to perform the first action (e.g., submit the content) without performing the activity (e.g., the user may check a box indicating that the user still wants to submit the content and that the user is willing to fully accept the potential negative consequences of submitted the content). In an example, the user may be provided with the override option only for certain classifications of content. In an example, the user may be provided with the override option only for content having a certain lower threshold of severity of a consequence of the content being submitted (e.g., override may be allowed for potentially annoying someone or hurting someone's feelings, as opposed to job loss where no override option is provided). In an example, the user may be provided with the override option only for content having a lower likelihood of a consequence actually occurring from the content being submitted (and/or consumed while the user has the emotional state).

Various types and/or combinations of activities may be populated within the user interface. In an example, one or more activities may be selected based upon the emotional state of the user, the first classification and/or the first sentiment. For example, a first activity (e.g., a cool off period with varying degrees of cool off times that are based upon (i) a severity of the emotional state of the user such as where the user must wait longer the angrier the user is determined to be and/or (ii) a classification of the content such as where the user must wait longer if the first classification indicates that the first content is a message to the user's boss than if the first classification indicates that the first content is a private social media message to a social media account) may be used for angry messages. A second activity (e.g., obtaining approval from a second user) and a third activity (e.g., having the user watch a video about people losing their jobs from posting racist social network posts) may be used for racist social network posts. In this way, activities may be selected based upon the emotional state of the user, the first classification and/or the first sentiment. In another example, one or more activities may be randomly selected. In another example, one or more activities may be selected based upon a severity of a consequence of the content being submitted and/or consumed (e.g., job loss, public shaming, annoying someone, hurting someone's feelings, or other consequences may be used to determine which activities to implement and parameters of the activities such as a number of questions that must be answered, a complexity of a puzzle, a length of the cool off period, etc.) and/or a severity of the conflict. In an example, one or more activities may be selected based upon a likelihood of a consequence actually occurring from the content being submitted. In some examples, the user may be provided with the option to submit the content based upon determining that the user successfully performed the activity. Alternatively and/or additionally, the user may be blocked from performing the first action (e.g., submitting the content for access by other users) before performing the activity.

In some examples, the communication system 502 may identify one or more problematic sections of content (e.g., the first content, the second content and/or other content). The content may comprise at least one of a message, an email, a social media post, etc. (created by the user, for example) that is not yet submitted for access by other users. Alternatively and/or additionally, the content may be consumed by the user. In some examples, the one or more problematic sections may comprise one or more sections that are deemed to potentially result in one or more negative consequences (e.g., at least one of job loss, shame, annoyance, or hurt feelings) if the content with the one or more problematic sections (i) was consumed by the user having the emotional state and/or (ii) was sent to one or more other users. For example, the one or more problematic sections may comprise language deemed to be at least one of offensive, racist, annoying, etc. In some examples, the communication n system 502 may evaluate the content to identify the one or more problematic sections and/or may display (via the second communication interface, for example) one or more representations of the one or more problematic sections in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments. In some examples, the replacement content is generated based upon the one or more problematic sections (e.g., the replacement content may be generated, by the generative AI tool, to be a replacement for the one or more problematic sections).

In some examples, the communication system 502 may control an unsend duration of time associated with content (e.g., at least one of a message, an email, a social media post, etc. created by the user using the second communication interface) and/or the second communication interface based upon the emotional state of the user, the first classification and/or the first sentiment. In some examples, the communication system 502 may adjust and/or update the unsend duration of time in response to (i) detecting a change to the emotional state, (ii) identifying the first conflict associated with the first classification and/or the emotional state (iii) determining that the emotional state of the user matches an emotional state of the set of triggering emotional states, (iv) determining that the first classification matches a classification of the set of triggering classifications, and/or (v) determining that the first sentiment matches a sentiment of the set of triggering sentiments. The communication system 502 may receive a request to provide the content to one or more other users (e.g., a request to send the message to a messaging contact, a request to send an email to one or more email addresses, a request to post a social network post on social network platform, etc.). In some examples, in response to receiving the request, the communication system 502 may provide the user with an option to unsend the content within the unsend duration of time. In some examples, in response to determining that the emotional state of the user is balanced and/or happy, the communication system 502 may set the unsend duration of time to a first (lower) value, such as about two seconds. In some examples, in response to determining that the emotional state of the user is angry, the communication system 502 may extend the unsend duration of time from the first value to a second (higher) value, such as about ten seconds. Thus, the user may be provided with a longer duration of time to reconsider sending content when the user is angry as compared to when the user is balanced and/or happy. In some examples, the second communication interface may display an indication of the unsend duration of time (and/or an indication that the unsend duration of time was extended or shortened) in response to adjusting and/or updating the unsend duration of time.

The one or more adaptive actions may comprise implementation of a delay or barrier so that the user has additional time to think through sharing and/or consuming content (e.g., at least one of a message, an email, a social media post, etc. created and/or consumed by the user using the second communication interface) so that the user may consider canceling the content and/or modifying the content (and/or consuming the content at a later time). For example, the delay or barrier may be triggered in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments. In an example, the delay or barrier may comprise (i) displaying one or more warnings indicative of a potential risk associated with sharing and/or consuming the content (e.g., potential job loss, shame, annoyance, hurt feelings, etc.), (ii) displaying a representation of the set of recommended actions, (iii) requesting that the user confirm they understand the potential risk and/or the set of recommended actions (and/or the user may be blocked from performing the first action prior to receiving the confirmation, that they understand the potential risk and/or the set of recommended actions, such as via selection of a selectable input), (iii) generate and/or display a user interface populated with an activity (e.g., a puzzle, a game, etc.), etc.

Figure 5B:
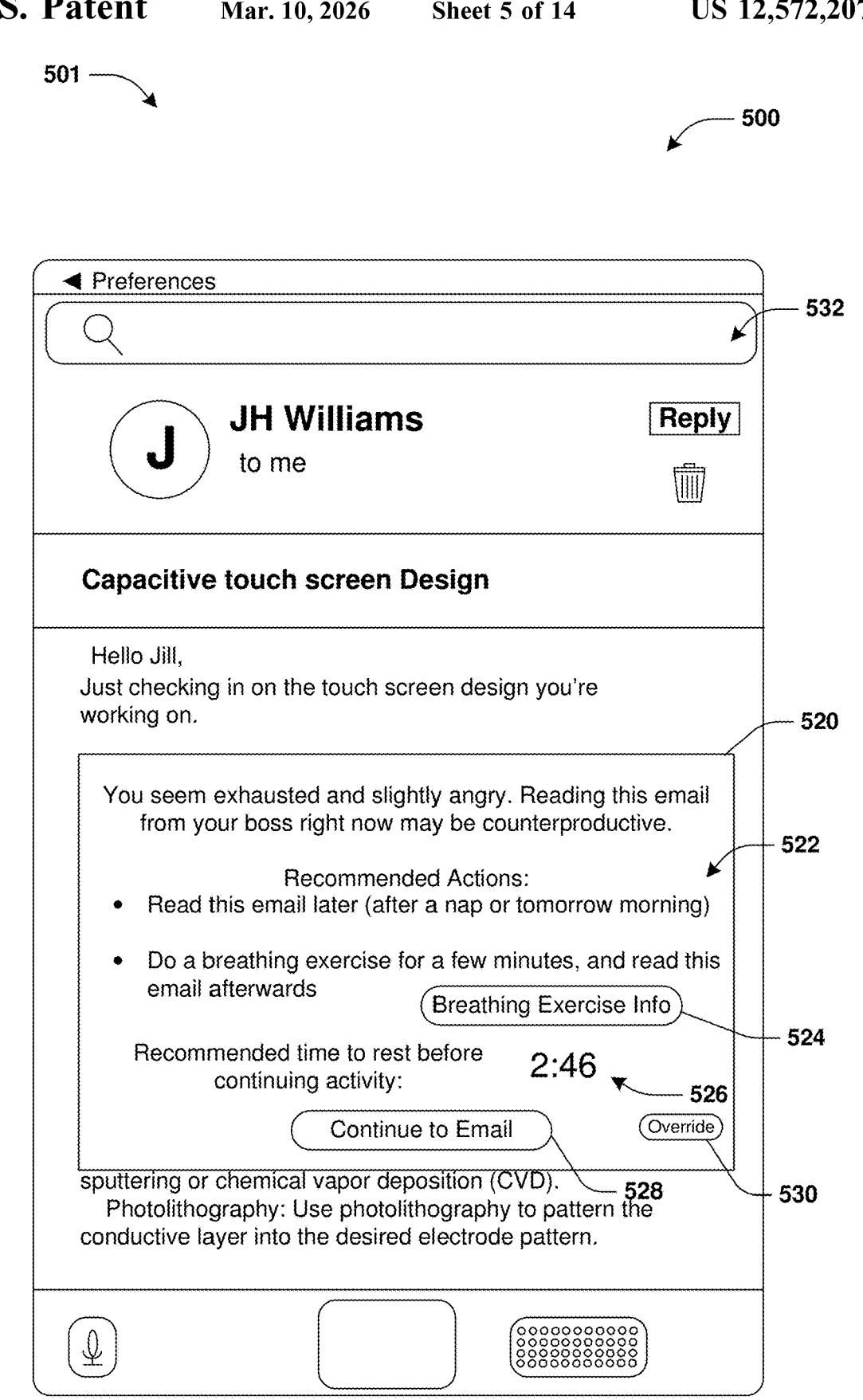
FIG. 5B is a component block diagram illustrating an example system for controlling a communication interface based upon an emotional state of a user, where a second communication interface is displayed via a first client device.

FIG. 5B illustrates an example in which the second communication interface displayed via the first client device (shown with reference number 500) comprises an email interface 532 displaying an email sent to the user (e.g., the email was sent to an email address of the user and/or was included in an inbox of the user). The first classification (e.g., a classification of the email) may indicate that the email is an email from the user's boss. The emotional state of the user may indicate that the user is exhausted and/or angry. The communication system 502 may trigger generation and/or display of a user interface 520 (via the second communication interface, for example) in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments. The user interface 520 may be populated with (i) an indication of the emotional state of the user, (ii) a representation 522 of one or more recommended actions (e.g., the set of recommended actions), (iii) a selectable input 524 for accessing one or more resources for a recommended action of the one or more recommended actions (e.g., a selection of the selectable input 524 may trigger display of text, audio, and/or a video teaching one or more breathing exercise methods and/or other relaxing techniques), (iv) a time left indicator 526 indicative of a time remaining until a cool off period the user is to wait before reading the email (e.g., the time left indicator 526 may decrease towards 0 with passage of time after the cool off period is initiated), (v) a resume activity selectable input 528 for removing the user interface 520 and/or resuming reading the email (e.g., the email may be displayed in unobstructed form in response to a selection of the resume activity selectable input 528), and/or (vi) a cool off period override selectable input 530. In some examples, the resume activity selectable input 528 may be inactive (and/or unselectable) prior to completion of the cool off period. Alternatively and/or additionally, the cool off period override selectable input 530 may be selected to remove the user interface 520 and/or resume reading the email prior to completion of the cool off period.

FIG. 5C illustrates an example in which the second communication interface displayed via the first client device 500 comprises an email compose interface 534 displaying text areas 536, 538 and/or 540 for inputting a set of recipients of an email being composed by the user, a subject of the email and/or an email body of the email. The email compose interface 534 may comprise a compose selectable input 546 for sending the email to an intended recipient (e.g., the user's coworker). The user may input email body text 548 (e.g., the user may type and/or create the email body text 548 using at least one of the touchscreen, the conversational interface, the keyboard, etc.). The first classification (e.g., a classification of the email) may indicate that the email is an email to the user's coworker. The emotional state of the user may indicate that the user is angry. The communication system 502 may evaluate the email body text 548 to identify one or more problematic sections of the email body text 548 and/or may generate and/or display one or more representations 542 and/or 544 of the one or more problematic sections. In some examples, the one or more problematic sections may be at least one of highlighted, displayed with a different font than other text of the email body text 548, outlined with a border (such as shown in FIG. 5C), etc. to distinguish the one or more problematic sections from other parts of the email body text 548. In some examples, the communication system 502 may generate replacement content (using the generative AI tool, for example) based upon the email body text 548, the one or more problematic sections, the first classification and/or the first sentiment. In some examples, the generative AI tool generates the replacement content based upon a prompt (e.g., a set of guidance information) input to the generative AI tool, wherein the prompt may comprise (i) the email body text 548, (ii) an indication of the first classification associated with the email body text 548, (iii) an indication of the first sentiment associated with the email body text 548, (iv) an indication of the emotional state of the user and/or (v) instructions based upon which the generative AI tool may generate the replacement content (e.g., an instruction to rephrase the input set of content to generate the replacement content to be written in a more professional manner than the email body text 548). In some examples, the email compose interface 534 may display a rephrase content selectable input 550 to generate and/or be provided with the replacement content. In some examples, the communication system 502 may trigger generation and/or display of the replacement content, the one or more representations 542 and/or 544, and/or the rephrase content selectable input 550 in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments.

In an example shown in FIG. 5D, the communication system 502 may trigger generation and/or display of a user interface 560 (overlaying the email compose interface 534, for example) populated with (i) a message 561 indicative of the emotional state of the user, the first classification and/or one or more negative consequences associated with sending the email, (ii) a representation 562 of one or more recommended actions (e.g., the set of recommended actions), (iii) a selectable input 564 for accessing one or more resources for a recommended action of the one or more recommended actions (e.g., a selection of the selectable input 564 may trigger display of text, audio, and/or a video teaching one or more breathing exercise methods and/or other relaxing techniques), (iv) an activity selectable input 563 for accessing an activity (e.g., a puzzle, a game, a video, etc.), (v) a rephrase content selectable input 565, (vi) a time left indicator 566 indicative of a time remaining until a cool off period the user is to wait before reading the email (e.g., the time left indicator 566 may decrease towards 0 with passage of time after the cool off period is initiated), (v) a resume activity selectable input 568 for removing the user interface 560 and/or resuming composing and/or sending the email (e.g., the email compose interface 534 may be displayed in unobstructed form in response to a selection of the resume activity selectable input 568), and/or (vi) a cool off period override selectable input 570. In some examples, the resume activity selectable input 568 may be inactive (and/or unselectable) prior to completion of the cool off period. In some examples, the communication system 502 may trigger generation and/or display of the user interface 560 (via the second communication interface, for example) in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments.

In an example shown in FIG. 5E, the communication system 502 may display a representation of the replacement content (shown with reference number 572). For example, the communication system 502 may populate text area 540 with the replacement content 572. In an example, the communication system 502 may display the representation of the replacement content 572 (and/or may replace the email body text 548 with the replacement content 572 in the text area 540) in response to a selection of the rephrase content selectable input 550 and/or the rephrase content selectable input 565. In an example, the user may select the compose selectable input 546 to send an email comprising the replacement content 572 to the user's coworker.

In an example shown in FIG. 5F, in response to receiving a request to send the email body text 548 (in response to a selection of the compose selectable input 546 without replacing the email body text 548 with the replacement content 572, for example), the communication system 502 may provide a user interface 511 populated with (i) a warning 513 that sending the email body text 548 could result in negative consequences, (ii) an indication 515 that the unsend duration of time is extended from 5 seconds to 20 seconds (e.g., the unsend duration of time may be extended based upon the first conflict, the first classification, the emotional state of the user and/or the one or more problematic sections), (iii) a selectable input 517 for requesting not to send the email body text 548 and/or (iv) a selectable input 519 for requesting to send the email body text 548 in an email. In some examples, in response to a selection of the selectable input 519, the communication system 502 may provide the user with the option to unsend (and/or recall) the email comprising the email body text 548 (e.g., the second communication interface may display an unsend selectable input in response to the selection of the selectable input 519, wherein the unsend selectable input may be selectable for at least the unsend duration of time and/or wherein selection of the unsend selectable input triggers the email comprising the email body text 548 to be recalled). Thus, the user may be provided with a longer duration of time to reconsider sending content when the user is angry as compared to when the user is balanced and/or happy. In some examples, the second communication interface may display an indication of the unsend duration of time (and/or an indication that the unsend duration of time was extended or shortened) in response to adjusting and/or updating the unsend duration of time.

Figure 5G:
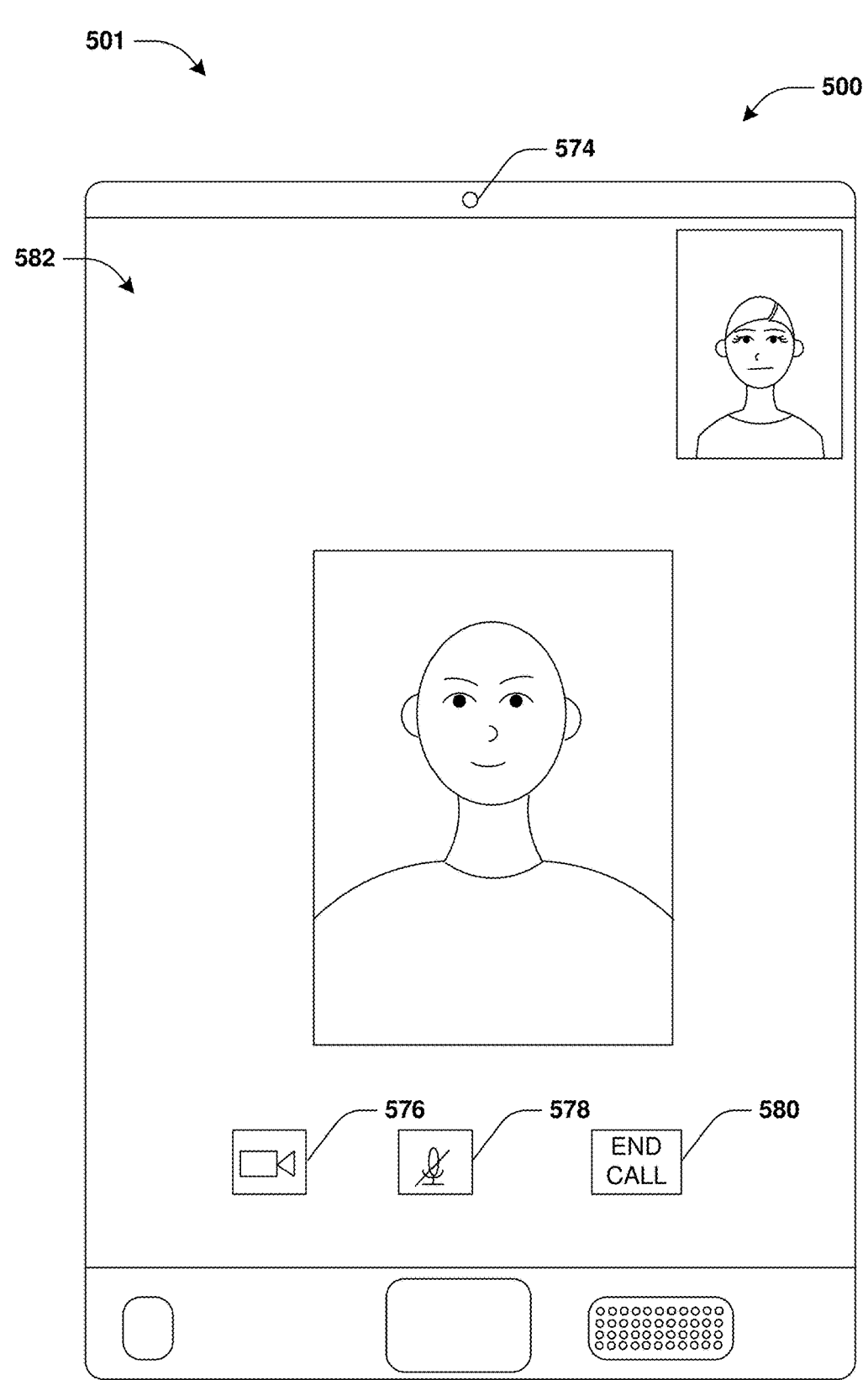
FIG. 5G is a component block diagram illustrating an example system for controlling a communication interface based upon an emotional state of a user, where a second communication interface is displayed via a first client device.

In an example shown in FIG. 5G, the second communication interface may comprise a calling interface 582 used to establish a call (e.g., a video call) between the user and one or more other users. Embodiments are contemplated in which the call comprises another type of call other than a video call (e.g., at least one of a VOIP call, a telephone call, a virtual call, etc.). The second communication interface may comprise a video selectable input 576 for activating and/or deactivating a camera 574 for the call, a mute selectable input 578 for muting the user's microphone for the call and/or an end call selectable input 580 for leaving the call.

In an example, the emotional state of the user may be determined to be angry, aggravated and/or agitated, which may be determined based upon a voice intensity level of the user during the call and/or a facial expression of the user during the call (and/or based upon other information). In an example, the first classification (e.g., a classification of the call) may indicate that the call is a call with the user's boss. In some examples, the communication system 502 may perform one or more mitigating actions in response to (i) identifying the first conflict associated with the first classification and/or the emotional state (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments. Alternatively and/or additionally, the one or more mitigating actions may be performed in response to evaluating audio of the call to determine that at least one of (i) speech patterns of the user and/or one or more other users indicate that the user and/or one or more other users are agitated or other emotional state, (ii) multiple participants of the call are interrupting each other, (iii) one or more participants of the call (e.g., the user) is using offensive language, etc. The one or more mitigating actions may comprise at least one of (i) automatically leaving the call, (ii) automatically muting the user's microphone for the call, (iii) automatically deactivating the camera 574 for the call, (iv) displaying a user interface 584, and/or (v) displaying a user interface 596.

In an example shown in FIG. 5H, the second communication interface may display the user interface 584 which may be populated with (i) an indication of the emotional state of the user, (ii) a representation 586 of one or more recommended actions (e.g., the set of recommended actions), (iii) a selectable input 588 for leaving the call, (iv) a selectable input 590 for accessing one or more resources for a recommended action of the one or more recommended actions (e.g., a selection of the selectable input 590 may trigger display of text, audio, and/or a video teaching one or more breathing exercise methods and/or other relaxing techniques), (v) a mute selectable input 591 for muting the user's microphone for the call, (vi) a disable video selectable input 592 for deactivating the camera 574 for the call, and/or (vi) a continue to call selectable input 594 for removing the user interface 584 and/or resuming the call.

In an example shown in FIG. 5I, the communication system 502 may automatically end the call for the user and/or may display the user interface 596 which may be populated with (i) a message 598 indicative of the emotional state (e.g., very angry) of the user, the first classification and/or one or more negative consequences associated with sending the email and/or a message 581 indicating that the call is ended for the user (e.g., the user is disconnected from the call), (ii) a representation 599 of one or more recommended actions (e.g., the set of recommended actions), (iii) a selectable input 583 for accessing one or more resources for a recommended action of the one or more recommended actions (e.g., a selection of the selectable input 583 may trigger display of text, audio, and/or a video teaching one or more breathing exercise methods and/or other relaxing techniques), (iv) an activity selectable input 585 for accessing an activity (e.g., a puzzle, a game, a video, etc.), (v) a time left indicator 587 indicative of a time remaining until a cool off period the user is to wait before rejoining the call, (v) a rejoin call selectable input 589 for removing the user interface 596 and/or resuming composing and/or sending the email (e.g., the email compose interface 534 may be displayed in unobstructed form in response to a selection of the rejoin call selectable input 589), and/or (vi) a cool off period override selectable input 593. In some examples, the rejoin call selectable input 589 may be inactive (and/or unselectable) prior to completion of the cool off period. In some examples, the one or more mitigating actions may include automatically ending the call (such as shown in FIG. 5I) for the user based upon a severity associated with the emotional state (e.g., a severity of anger) of the user exceeding a threshold severity. In some examples, the one or more mitigating actions may include not automatically ending the call (such as shown in FIG. 5H) for the user based upon a severity associated with the emotional state (e.g., a severity of anger) of the user not exceeding the threshold severity.

Figure 5J:
FIG. 5J is a component block diagram illustrating an example system for controlling a communication interface based upon an emotional state of a user, where a second communication interface is displayed via a first client device.

FIG. 5J illustrates an example in which the second communication interface displayed via the first client device 500 comprises the email compose interface 534 displaying text areas 536, 538 and/or 540 for inputting information of an email being composed by the user. The user may input an intended recipient (e.g., the user's spouse) in the text area 536. The user may input email body text 549 (e.g., the user may type and/or create the email body text 549 using at least one of the touchscreen, the conversational interface, the keyboard, etc.). The first classification (e.g., a classification of the email) may indicate that the email is flowery and/or is an email to the user's spouse. The emotional state of the user may indicate that the user is angry. The communication system 502 may evaluate the email body text 549 to identify one or more problematic sections of the email body text 549 and/or may generate and/or display a representation 543 of the one or more problematic sections. In some examples, the one or more problematic sections may be at least one of highlighted, displayed with a different font than other text of the email body text 549, outlined with a border (such as shown in FIG. 5J), etc. to distinguish the one or more problematic sections from other parts of the email body text 549. In some examples, the one or more problematic sections may comprise a section that is determined to be overly descriptive compared with past emails (and/or other types of messages) the user sent to their spouse, which may cause the user's spouse to become worried if the spouse feels the email body text 549 includes unusual language that is not to be expected from the user. In some examples, the communication system 502 may generate replacement content (using the generative AI tool, for example) based upon the email body text 549, the one or more problematic sections, the first classification and/or the first sentiment. In some examples, the generative AI tool generates the replacement content based upon a prompt (e.g., a set of guidance information) input to the generative AI tool, wherein the prompt may comprise (i) the email body text 549, (ii) an indication of the first classification associated with the email body text 549, (iii) an indication of the first sentiment associated with the email body text 549, (iv) an indication of the emotional state of the user and/or (v) instructions based upon which the generative AI tool may generate the replacement content (e.g., an instruction to shorten and/or remove the one or more problematic sections such that the email body text 549 is more typical of the user's past behavior). In some examples, the email compose interface 534 may display a rephrase content selectable input 551 to generate and/or be provided with the replacement content. In some examples, the communication system 502 may trigger generation and/or display of the replacement content, the representation 543, and/or the rephrase content selectable input 551 in response to (i) identifying the first conflict between the first classification indicating that the email is flowery and the emotional state of the user being angry, which may indicate that the user is unbalanced and/or is struggling to write the email in a normal manner they typically write their emails and instead may be overcompensating for the anger, (ii) determining that the emotional state of the user matches an emotional state of the set of triggering emotional states, (iii) determining that the first classification matches a classification of the set of triggering classifications, and/or (iv) determining that the first sentiment matches a sentiment of the set of triggering sentiments.

Alternatively and/or additionally, the communication system 502 may determine the emotional state based upon a detected difference between expected behavior of the user and the first user activity. For example, the trained emotional state prediction model may learn (based upon the set of training information, for example) that the user normally speaks with her spouse using a first channel (a first instant messaging application). Thus, the trained emotional state prediction model may determine that the user is unbalanced (and/or that the emotional state of the user is associated with a negative emotion) based upon the user using a different channel (e.g., an email application that displays the email compose interface 534) to communicate with her spouse than the first channel. In some examples, the communication system 502 may control an interface of the first instant messaging application and an interface of the email application using one, some and/or all of the techniques provided herein with respect to controlling the second communication interface.

In some examples, the trained emotional state prediction model is trained and/or updated over time using (i) subsequently detected user activity, (ii) subsequently collected signals (sensor-based signals), and/or (iii) feedback, such as user responses by the user to user interface adjustments made based upon the emotional state. In an example, the trained emotional state prediction model may be trained to such a point that the trained emotional state prediction model is able to determine the emotional state merely using one or more first types of information (e.g., sensor-based information, user activity, etc.) and not using one or more second types of information (e.g., sensor-based information, user activity, etc.). For example, in a scenario when sensor-based information is available to the communication system 502 but user activity information is not available to the communication system 502, the trained emotional state prediction model may determine the emotional state using merely the sensor-based information (and/or not using the user activity information). In an example, in a scenario when user activity information is available to the communication system 502 but sensor-based information is not available to the communication system 502, the trained emotional state prediction model may determine the emotional state using merely the user activity information (and/or not using the sensor-based information).

In some examples, each machine learning model of one, some and/or all machine learning models of the present disclosure (e.g., at least one of the trained emotional state prediction model, one or more machine learning models of the generative AI tool, etc.) may comprise at least one of a generative artificial intelligence (AI) tool, a neural network, a tree-based model, a machine learning model used to perform linear regression, a machine learning model used to perform logistic regression, a decision tree model, a support vector machine (SVM), a Bayesian network model, a k-Nearest Neighbors (k-NN) model, a K-Means model, a random forest model, a machine learning model used to perform dimensional reduction, a machine learning model used to perform gradient boosting, etc.

In an example, the user may have an audible argument in a physical location where they are based which may be captured by the audio signal. The communication system may detect the user arguing and/or becoming angry based upon the voice intensity level meeting (e.g., exceeding or being less than) a threshold voice intensity level or within a defined range of voice intensity levels and/or speech patterns of the user. One or more of the operations of the present disclosure may be triggered based upon the detection of the user arguing and/or becoming angry (e.g., trigger a delay or barrier so that the user has additional time to think through sharing and/or consuming content).

Other types of interfaces of the second communication interface other than those shown in and/or described with respect to FIGS. 5B-5J are within the scope of the present disclosure. The second communication interface may comprise an email interface, a text messaging interface, an instant messaging interface, a social network interface, a blog, a content interface for viewing and/or downloading content items (e.g., videos, images, links, audio, articles, etc.) and/or other type of interface.

In some examples, one, some and/or all operations of the present disclosure may be performed by an application (e.g., a web application, a mobile application, etc.) on the first client device 500. In some examples, one, some and/or all operations of the present disclosure may be performed by an operating system of the first client device 500. Alternatively and/or additionally, one, some and/or all operations of the present disclosure may be performed by a server (e.g., hosting a service accessible via a network, such as the Internet) that may be connected to the first client device 500.

It may be appreciated that the disclosed subject matter may assist a user in optimizing their behavior while using one or more applications (e.g., communication applications).

Implementation of at least some of the disclosed subject matter may lead to benefits including a reduction in screen space and/or an improved usability of a display (e.g., of a client device) (e.g., as a result of automatically identifying one or more problematic sections of content and/or automatically generating and/or providing the replacement content based upon the one or more problematic sections).

Alternatively and/or additionally, implementation of at least some of the disclosed subject matter may lead to benefits including less manual effort (e.g., as a result of generating the replacement content automatically, wherein manual editing to produce the replacement content is not required).

In some examples, the second communication interface (and/or the first client device 500) is configured to display a menu listing one or more features (e.g., selectable features) of the communication system 502. The one or more features may comprise at least one of a search feature, a content feature, a messaging feature, a social network feed feature, etc. In an example, in response to a selection of the search feature, the search feature may provide one or more resources for using a search engine of the communication system 502 to search for content. In an example, in response to a selection of the content feature, the content feature may provide one or more resources for displaying and/or engaging with content items (e.g., videos, images, audio files, news articles, etc.). In response to a selection of the messaging feature, the messaging feature may provide one or more resources (e.g., data, an interface, etc.) for displaying and/or facilitating messaging conversations (e.g., private messaging conversations and/or public messaging conversations) between users of the communication system 502 (e.g., users of the communication system 502 may send messages to each other using the messaging feature of the communication system 502). In response to a selection of the social network feed feature, the social network feed feature may provide one or more resources (e.g., data, an interface, etc.) for displaying social network posts and/or comments on a social network platform. In some examples, the client device is configured to display a content platform application summary that can be reached directly from the menu, wherein the content platform application summary displays a limited list of data offered within the one or more features. In some examples, each of the data in the limited list of data is selectable to launch the respective feature (of the one or more features) and enable the selected data to be seen within the respective feature. In some examples, the content platform application summary is displayed while the one or more features are in an un-launched and/or unopened state.

In some examples, at least some of the disclosed subject matter may be implemented on a client device, and in some examples, at least some of the disclosed subject matter may be implemented on a server (e.g., hosting a service accessible via a network, such as the Internet).

Figure 6:
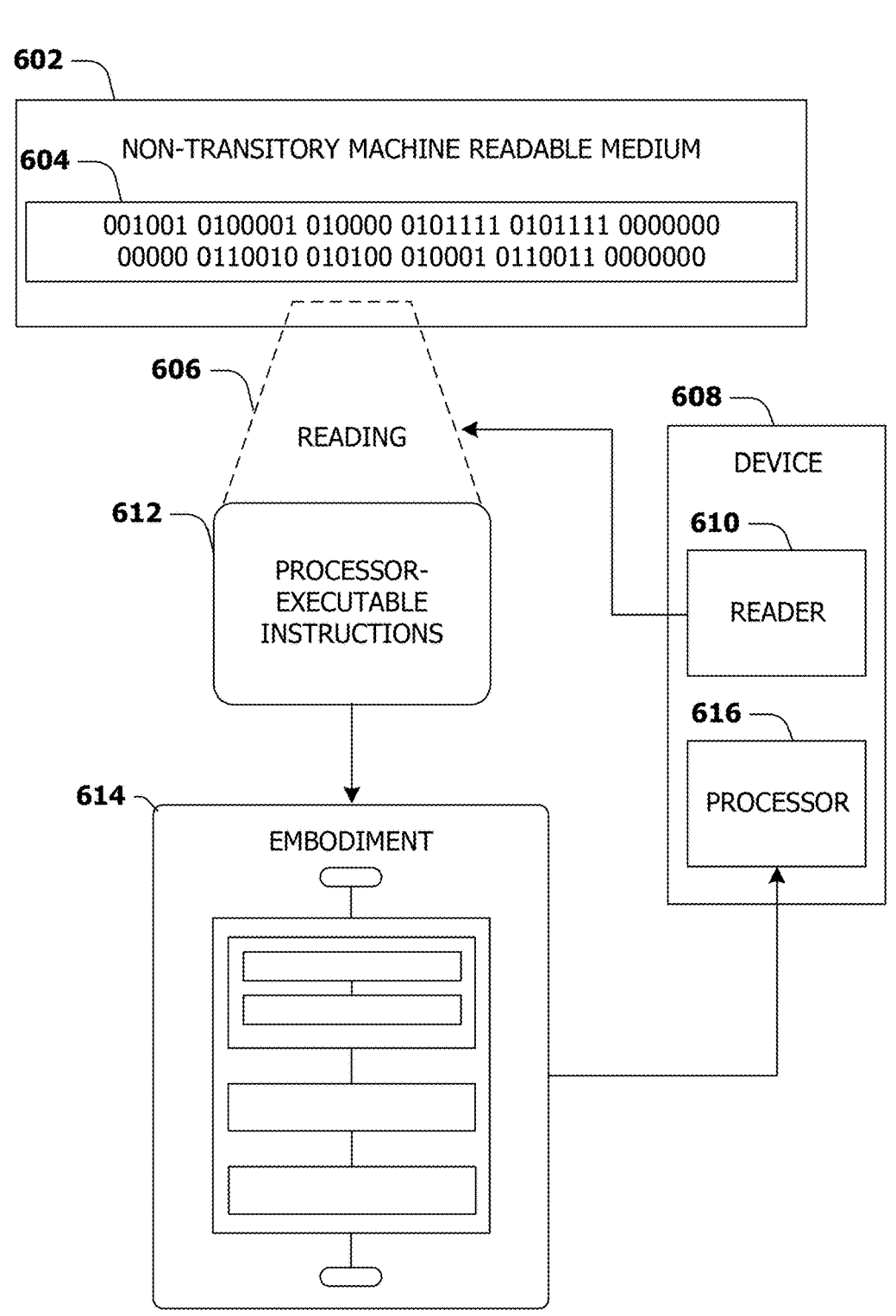
FIG. 6 is an illustration of a scenario featuring an example non-transitory machine readable medium in accordance with one or more of the provisions set forth herein.

FIG. 6 is an illustration of a scenario 600 involving an example non-transitory machine readable medium 602. The non-transitory machine readable medium 602 may comprise processor-executable instructions 612 that when executed by a processor 616 cause performance (e.g., by the processor

616) of at least some of the provisions herein (e.g., embodiment 614). The non-transitory machine readable medium 602 may comprise a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a compact disc (CD), digital versatile disc (DVD), or floppy disk). The example non-transitory machine readable medium 602 stores computer-readable data 604 that, when subjected to reading 606 by a reader 610 of a device 608 (e.g., a read head of a hard disk drive, or a read operation invoked on a solid-state storage device), express the processor-executable instructions 612. In some embodiments, the processor-executable instructions 612, when executed, cause performance of operations, such as at least some of the example method 400 of FIG. 4, for example. In some embodiments, the processor-executable instructions 612 are configured to cause implementation of a system, such as at least some of the example system 501 of FIGS. 5A-5J, for example.

3. Usage of Terms

As used in this application, "component," "module," "system", "interface", and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "example" is used herein to mean serving as an instance, illustration, etc., and not necessarily as advantageous. As used herein, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", and/or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Various operations of embodiments are provided herein. In an embodiment, one or more of the operations described may constitute computer readable instructions stored on one or more computer and/or machine readable media, which if executed will cause the operations to be performed. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method, comprising:
determining an emotional state of a user based upon at least one of (i) one or more signals generated by one or more sensors, or (ii) user activity of the user;
evaluating content at least one of generated or identified by the user to determine a classification of the content;
determining an unsend duration of time based upon at least one of the classification or the emotional state; and
in response to receiving a request to provide the content to one or more other users, providing, via a communication interface, the user with an option to unsend the content within the unsend duration of time.

2. The method of claim 1, wherein determining the unsend duration of time is performed based upon the classification.

3. The method of claim 1, comprising:
generating, using a generative artificial intelligence (AI) tool, replacement content based upon at least one of the emotional state, the classification, or the content; and
at least one of:
displaying a representation of the replacement content; or
providing the user with an option to replace the content with the replacement content.

4. The method of claim 1, wherein determining the unsend duration of time is performed based upon the emotional state.

5. The method of claim 1, comprising:
in response to identifying a conflict between the classification of the content and the emotional state of the user, displaying a user interface populated with one or more recommended actions.

6. The method of claim 5, wherein the one or more recommended actions comprise at least one of:
postponing consumption of the content;
postponing transmission of the content to one or more other users; or
rephrasing the content.

7. The method of claim 1, comprising:
in response to identifying a conflict between the classification of the content and the emotional state of the user, displaying a user interface populated with at least one of (i) an activity for the user to perform or (ii) instructions for the activity.

8. The method of claim 7, comprising:
generating at least one of a puzzle, a game, or a math problem as the activity.

9. The method of claim 7, wherein the activity comprises a cool off period the user is to wait before being able to initiate an action associated with the content.

10. The method of claim 1, wherein the content comprises at least one of an email, a text message, a social network message, a social network post, a video post, an image, a social network comment on a post, a video call, a voice call, or a link to external content.

11. The method of claim 1, comprising:
displaying a user interface populated with one or more recommended actions comprising at least one of:
a relaxing action;
muting an ongoing call;
leaving the ongoing call; or
rejoining the ongoing call at a later time.

12. The method of claim 1, comprising:
training a machine learning model to generate a trained emotional state prediction model using a set of training information comprising at least one of (i) one or more historical emotional states associated with the user, (ii) historical user activity associated with the user, or (iii) historical sensor-based information associated with the user, wherein the emotional state of the user is determined using the trained emotional state prediction model.

13. The method of claim 1, wherein the one or more signals comprise at least one of:
one or more biometric signals indicative of one or more biometric parameters associated with the user;
an image signal indicative of an image comprising a view of the user; and
an audio signal indicative of audio associated with the user.

14. A non-transitory machine-readable medium having stored thereon processor-executable instructions that when executed cause performance of operations, the operations comprising:
determining an emotional state of a user based upon at least one of (i) one or more signals generated by one or more sensors, or (ii) user activity of the user;

evaluating content at least one of generated or identified by the user to determine a classification of the content;

generating, using a generative artificial intelligence (AI) tool, replacement content based upon at least one of the emotional state, the classification, or the content; and providing, via a communication interface, the user with an option to replace the content with the replacement content.

15. The non-transitory machine-readable medium of claim 14, wherein generating the replacement content is performed based upon the content.

16. The non-transitory machine-readable medium of claim 14, wherein generating the replacement content is performed based upon the classification.

17. The non-transitory machine-readable medium of claim 14, the operations comprising:

determining an unsend duration of time based upon at least one of the classification or the emotional state; and in response to receiving a request to provide the content to one or more other users, providing the user with an option to unsend the request within the unsend duration of time.

18. A computing device comprising:

a processor; and memory comprising processor-executable instructions that when executed by the processor cause performance of operations, the operations comprising:

determining an emotional state of a user based upon at least one of (i) one or more signals generated by one or more sensors, or (ii) user activity of the user;

evaluating content at least one of generated or identified by the user to determine a classification of the content;

generating, using a generative artificial intelligence (AI) tool, replacement content based upon at least one of the emotional state, the classification, or the content; and displaying, via a communication interface, a representation of the replacement content.

19. The computing device of claim 18, wherein generating the replacement content is performed based upon the content.

20. The computing device of claim 18, wherein generating the replacement content is performed based upon the classification.

\* \* \* \* \*